US011839450B2

(12) United States Patent
Montgomery, II et al.

(10) Patent No.: US 11,839,450 B2
(45) Date of Patent: Dec. 12, 2023

(54) PRESSURE SENSOR MODULE FOR WEARABLE APPLANATION TONOMETER

(71) Applicant: Apple Inc., Cupertino, CA (US)

(72) Inventors: Robert K. Montgomery, II, Cupertino, CA (US); Chin San Han, Mountain View, CA (US); Pablo A. Escobar, San Francisco, CA (US); Zijing Zeng, San Jose, CA (US)

(73) Assignee: Apple Inc., Cupertino, CA (US)

( * ) Notice: Subject to any disclaimer, the term of this patent is extended or adjusted under 35 U.S.C. 154(b) by 244 days.

(21) Appl. No.: 17/030,234

(22) Filed: Sep. 23, 2020

(65) Prior Publication Data

US 2022/0087541 A1 Mar. 24, 2022

(51) Int. Cl.
*A61B 5/0205* (2006.01)
*G01L 27/00* (2006.01)
*G01L 9/00* (2006.01)
*G01L 19/06* (2006.01)
*A61B 5/00* (2006.01)
*A61B 5/02* (2006.01)
*A61B 5/16* (2006.01)
*G01L 19/00* (2006.01)
*A61B 5/021* (2006.01)
*A61B 5/024* (2006.01)
*A61B 5/08* (2006.01)

(52) U.S. Cl.
CPC ........ *A61B 5/0205* (2013.01); *A61B 5/02007* (2013.01); *A61B 5/165* (2013.01); *A61B 5/4809* (2013.01); *A61B 5/681* (2013.01); *A61B 5/6815* (2013.01); *G01L 9/0051* (2013.01); *G01L 19/0092* (2013.01); *G01L 19/0618* (2013.01); *G01L 27/002* (2013.01); *A61B 5/024* (2013.01); *A61B 5/02125* (2013.01); *A61B 5/0816* (2013.01); *A61B 2560/0223* (2013.01); *A61B 2562/0247* (2013.01); *A61B 2562/043* (2013.01); *A61B 2562/046* (2013.01)

(58) Field of Classification Search
CPC ... A61B 5/0205; A61B 5/02007; A61B 5/681; A61B 5/6815; A61B 5/024; A61B 2562/0247
See application file for complete search history.

(56) References Cited

U.S. PATENT DOCUMENTS

| 5,437,189 A | 8/1995 | Brown et al. |
| 6,401,545 B1 * | 6/2002 | Monk ................. G01L 19/0627 73/756 |
| 6,441,503 B1 | 8/2002 | Webster |

(Continued)

OTHER PUBLICATIONS

U.S. Appl. No. 17/030,198, filed Sep. 23, 2020, Montgomery et al.
(Continued)

*Primary Examiner* — Michael W Kahelin
(74) *Attorney, Agent, or Firm* — Brownstein Hyatt Farber Schreck, LLP

(57) ABSTRACT

An interface pressure sensor includes a fluid pressure sensor disposed in a volume defined by a shear wall. The volume is enclosed, and the fluid pressure sensor is encapsulated by, an infill material. The infill material defines a sensing surface that, when pressed, can impart a force that is detectable by the fluid pressure sensor. The interface pressure sensor can be used for applanation tonometry.

11 Claims, 19 Drawing Sheets

(56) References Cited

U.S. PATENT DOCUMENTS

| | | |
|---|---|---|
| 7,305,888 B2 | 12/2007 | Walchli |
| 7,409,876 B2 | 8/2008 | Ganapathi et al. |
| 7,698,950 B2 | 4/2010 | Kraatz |
| 8,157,730 B2 | 4/2012 | LeBoeuf et al. |
| 8,922,380 B2 | 12/2014 | O'Connor |
| 9,254,995 B2 | 2/2016 | Bolognia et al. |
| 9,608,297 B2 | 3/2017 | van Lammeren et al. |
| 9,737,657 B2 | 8/2017 | Miesel et al. |
| 9,846,095 B2 | 12/2017 | Chiou et al. |
| 9,952,110 B2 | 4/2018 | Beer et al. |
| 10,371,591 B2 | 8/2019 | Wagner et al. |
| 10,599,101 B2 | 3/2020 | Rothkopf |
| 10,599,192 B2 | 3/2020 | Younes et al. |
| 10,610,157 B2 | 4/2020 | Pandya et al. |
| 10,684,708 B2 | 6/2020 | Zimmerman et al. |
| 10,720,534 B2 | 7/2020 | Tomita |
| 10,757,491 B1 | 8/2020 | Jackson et al. |
| 10,860,114 B1 | 12/2020 | Oommen et al. |
| 10,866,683 B2 | 12/2020 | Gupta et al. |
| 10,890,502 B2 | 1/2021 | Miyake et al. |
| 10,948,372 B2 | 3/2021 | Arndt et al. |
| 11,089,419 B2 | 8/2021 | Niederberger |
| 11,397,120 B2 | 7/2022 | Montgomery et al. |
| 11,419,504 B2 | 8/2022 | Nielsen et al. |
| 11,534,071 B2 | 12/2022 | Vule et al. |
| 11,624,667 B2 | 4/2023 | Montgomery et al. |
| 2011/0160597 A1* | 6/2011 | Lane .................. A61B 5/0225 600/493 |
| 2017/0067790 A1 | 3/2017 | Takeuchi |
| 2017/0209055 A1* | 7/2017 | Pantelopoulos ..... A61B 5/7203 |
| 2019/0078957 A1* | 3/2019 | Miyake ................. G01L 19/142 |
| 2019/0150754 A1 | 5/2019 | Naik et al. |
| 2019/0223736 A1 | 7/2019 | Wang et al. |
| 2020/0073504 A1* | 3/2020 | Deng .................... G06F 1/1637 |
| 2020/0163561 A1 | 5/2020 | Choe |
| 2021/0030367 A1 | 2/2021 | Cho et al. |
| 2021/0100513 A1 | 4/2021 | Bahmanyar et al. |
| 2021/0167487 A1 | 6/2021 | Varma et al. |
| 2021/0169417 A1* | 6/2021 | Burton ................. A61B 5/4857 |
| 2021/0219852 A1 | 7/2021 | Colburn et al. |
| 2021/0330261 A1 | 10/2021 | Jung et al. |
| 2021/0353164 A1* | 11/2021 | Chegani ............. A61B 5/02125 |
| 2022/0009438 A1 | 1/2022 | Schaller et al. |
| 2022/0087551 A1 | 3/2022 | Montgomery et al. |
| 2022/0087552 A1 | 3/2022 | Montgomery et al. |
| 2022/0087553 A1 | 3/2022 | Han et al. |
| 2022/0091569 A1 | 3/2022 | Montgomery et al. |

OTHER PUBLICATIONS

U.S. Appl. No. 17/030,247, filed Sep. 23, 2020, Han et al.
U.S. Appl. No. 17/030,265, filed Sep. 23, 2020, Montgomery et al.
U.S. Appl. No. 17/030,278, filed Sep. 23, 2020, Montgomery et al.
U.S. Appl. No. 17/030,317, filed Sep. 23, 2020, Montgomery et al.
Fassbender et al., "Simulation and characterization of encapsulated pressure sensors," *Procedia Chemistry* I, 2009, pp. 843-846.
Kato et al., "Sensor Technology to Realize Continuous Blood Pressure Monitoring," *Omron Technics*, vol. 50.004EN, 2019.3, 10 pages.
León et al., "Elastomer Encapsulated Pressure Sensor With Engineered Air Cavity for Force Sensing," *IEEE Sensors Journal*, vol. 19, No. 16, Aug. 15, 2019, pp. 6628-6643.
Mannsfeld et al., Highly sensitive flexible pressure sensors with microstructured rubber dielectric layers *Nature Materials*, vol. 9, Oct. 2010, pp. 859-864.
Tenzer et al., "Inexpensive and Easily Customized Tactile Array Sensors using MEMS Barometers Chips," IEEE 2012, 5 pages.

* cited by examiner

PRESSURE SENSOR MODULE FOR WEARABLE APPLANATION TONOMETER

TECHNICAL FIELD

Embodiments described herein relate to pressure sensing systems for electronic devices and, in particular, to systems and methods facilitating sampling pressure changes over time at an interface defined by an exterior surface of a pressure sensor module or electronic device housing.

BACKGROUND

An electronic device can include a force sensor. Conventional force sensors are typically implemented with compressible capacitive plates, piezoelectric materials, piezoresistive materials, strain-sensitive materials, and the like. However, in part as a direct result of these architectures and materials, conventional force sensors reserve substantial volume and/or area with an electronic device housing, and may not be readily or efficiently incorporated into portable or low-profile applications. In addition, conventional force sensors typically have structurally-limited and/or nonlinear force sensitivity that render such sensors unable to accurately or precisely detect small or gradual changes in force. Further still, many conventional high precision and high accuracy force sensors (which may be used in medical, scientific, or industrial applications) are typically delicate and/or expensive, requiring specialized training to install, service, and operate.

Due to these and other shortcomings, conventional force sensors are often not suitable for one or more of: (1) small form factor applications, such as in wearable electronic devices; (2) low-cost applications requiring durability, such as in sports equipment; or (3) high precision and high accuracy applications, such as in noninvasive medical devices.

SUMMARY

Embodiments described herein take the form of an interface pressure sensor system for an electronic device. The interface pressure sensor system defines a sensing surface configured to receive a normal force. The sensing surface forms a portion of a potting, infill, or encapsulation material disposed over, and enclosing, a microelectromechanical fluid pressure sensor. As a result of this construction, when the sensing surface receives a force, the encapsulation material transits that force, or at least a portion thereof, to a microelectromechanical force or pressure sensitive structure that deforms in response. A property of an electrical circuit conductively coupled to the microelectromechanical sensor can be converted into a force applied to the sensing surface. A surface area of the sensing surface can also be leveraged to determine a pressure applied to the interface pressure sensor system. In another phrasing, a force detected by the interface pressure sensor system can be divided by the surface area of the sensor to obtain a pressure measurement.

In many embodiments, an interface pressure sensor system includes a rigid module enclosure, which may also be referred to as a shear wall. The enclosure provides mechanical resistance against shear forces that may otherwise include a component normal to the sensing surface. As a result of this construction, an interface pressure sensor system as described herein is mechanically configured to measure pressure and/or force input oriented normal to the sensing surface.

More particularly, in many embodiments, an interface pressure sensor system includes a rigid module enclosure defining an interior volume. A (microelectromechanical) barometric or other fluid pressure sensor is disposed within the interior volume. In addition, an infill material (e.g., thermoset polymer, bismaleimide-triazine resin, other resins, plastics, epoxies, silica, silicone, polyimide, and so on) is disposed over the pressure sensor so as to fill the interior volume, encapsulate and protect the fluid pressure sensor, and to define an interface surface to receive pressure input.

Related and additional embodiments include a configuration in which the module enclosure defines a closed polygonal shape (e.g., rectangle, rhombus, hexagon, or other polygon) at least in part defining an interior perimeter of the interior volume.

Related and additional embodiments may include with a substrate, such as a rigid substrate, supporting the module enclosure. In such constructions, the fluid pressure sensor may be coupled to the substrate. The substrate may be formed from a material such as metal, plastic, ceramic, silica, and/or glass.

Further, embodiments described herein take the form of an interface pressure sensor system for detecting normal force to an interface surface. The interface pressure sensor system includes an outer module enclosure defining an outer volume, a set of interface sensor modules, each disposed within the outer volume. Each respective interface sensor module includes a module enclosure defining an interior volume, a pressure sensor disposed within the interior volume, and an infill material disposed over the pressure sensor and filling the interior volume. In addition, an outer module infill material fills the first volume and at least partially encloses the set of interface sensor modules within the outer volume. In another, non-limiting phrasing, an interface pressure sensor system as described herein can include two stages of module enclosures/shear walls. Namely, an outer shear wall/enclosure can provide a first amount of shear force resistance and an inner shear wall/enclosure can provide a second amount of shear force resistance.

Related and additional embodiments include a configuration in which the outer module infill defines a first interface surface and at least one respective infill material of at least one interface sensor modules of the set of sensor modules defines a second interface surface. The second interface surface can be flush with, inset with respect to, or proud of the first interface surface.

In some cases, a pressure sensor can be associated with a dedicated processor, microprocessor, and/or application-specific integrated circuit. In some cases, such electronic circuitry can be included within the same encapsulated interior volume as a pressure sensor to which that circuitry is coupled.

In one configuration, an interface pressure sensor system can include a set of interface sensor modules that, in turn, includes a first sensor module, a second sensor module, a third sensor module, and a fourth sensor module. Other numbers of sensors are possible; this is merely one example configuration. In a configuration, the first and second sensor modules can be disposed in a first row and the third and fourth sensor modules are disposed in a second row. In many implementations of this construction, the first row may be offset relative to the second row such that each sensor module is offset from a nearest sensor module by a selected pitch. As a result of this construction, the interface sensing system has improved linear position tolerance.

Additional embodiments described herein take the form of a pressure sensing system. The pressure sensing system includes a substrate and a first frame (also referred to as a module enclosure, module housing, or shear wall) disposed on the substrate and defining a first interior volume. The pressure sensing system also includes a second frame defining a second interior volume. The second frame is disposed within the first interior volume, such that the first frame circumscribes the second frame.

In these constructions, the pressure sensing system further includes a third frame defining a third interior volume. As with the second frame, the third frame is disposed within the first interior volume and separated from the second frame by a distance or a pitch. In this manner, the first frame circumscribes both the second frame and the third frame.

As with other described and contemplated embodiments, the pressure sensing system can include a first pressure sensor disposed within the second interior volume. The first pressure sensor itself includes a first fluid pressure sensor and a first application-specific integrated circuit operably coupled to the first fluid pressure sensor and configured to generate a first output corresponding to pressure received by the first fluid pressure sensor.

In addition, the pressure sensing system includes a second pressure sensor disposed within the third interior volume and, as described above, includes a second fluid pressure sensor and a second application-specific integrated circuit operably coupled to the second fluid pressure sensor and configured to generate a second output corresponding to pressure received by the second fluid pressure sensor.

As with other described and contemplated embodiments, the pressure sensing system can include an infill or encapsulation material filling the first interior volume, the second interior volume, and the third interior volume to encapsulate the first pressure sensor and the second pressure sensor, the infill material defining an interface surface to receive pressure input. As a result of this construction, a pressure or force applied to the interface surface can be received by at least one of the first pressure sensor or the second pressure sensor.

Still further embodiments contemplate various example use cases of an interface pressure sensor system and/or interface pressure sensor system as described herein.

For example, some embodiments described herein take the form of an electronic device configured for biometric sensing. In such constructions, the electronic device can include at least a sensing surface configured to detect pressure variations deforming an external surface of an object (e.g., radial pulse of a user). The sensing surface can be defined at least in part by and an interface pressure sensor system, such as described herein.

In particular, in a configuration, the interface pressure sensor system includes at least a stiffener, a substrate supported by the stiffener, and a first pressure sensing module disposed on the substrate. The first pressure sensor can include a first frame coupled to the substrate and defining a first volume, a first fluid pressure sensor disposed within the first volume, and a first infill encapsulating the first fluid pressure sensor within the first volume and at least partially defining the sensing surface.

In addition, the interface pressure sensor system can further include a second pressure sensor module disposed on the substrate, offset from the first pressure sensing module and including: a second frame coupled to the substrate and defining a second volume; a second fluid pressure sensor disposed within the second volume; and a second infill encapsulating the first fluid pressure sensor within the second volume and at least partially defining the sensing surface. In this manner, both the first sensor module and the second sensor module define at least a portion of the sensing surface of the electronic device.

Related and additional embodiments may include a processor operably coupled to the interface pressure sensor system and operable to receive a first output from the first fluid pressure sensor, and receive a second output from the second fluid pressure sensor. The processor may be configured to determine an augmentation index of the user based on at least one of the first output or the second output. In other cases, the processor may be additionally or alternatively configured to determine at least one of a systolic or a diastolic blood pressure of the user based on at least one of the first output or the second output. In yet other cases, the processor may be configured to determine an arterial state of the user based on at least one of the first output or the second output.

In further embodiments, the electronic device can include a heartrate sensor operably coupled to the processor. In these constructions, the heartrate sensor can be configured to provide a third output corresponding to heart rate, respiration rate, and so on. In this example, the processor may be configured to determine a health parameter of the user based on the third output and at least one of the first output or the second output. In other words, the processor can be configured to leverage output(s) of multiple discrete sensors, whether health sensors or otherwise (e.g., accelerometers, gyroscopes, and so on), in order to inform determination of one or more health parameters such as augmentation index, chronological age, arterial age state, arterial disease state, user stress level, heart rate, respiration rate, pulse waveform velocity, other pulse waveform parameters, and so on.

Related and additional embodiments include a configuration in which the sensing surface defines at least a portion of an interior surface of a band worn on a user's wrist. In these constructions, the interface pressure sensor system can be configured to detect one or more pressure waves or pulse parameters based on pressure applied by the user's skin (as a result of expansion and contraction of the user's radial artery) against the sensing surface.

Some embodiments described herein take the form of an electronic device configured to detect a biometric parameter of a user. The electronic device can include an interface pressure sensor system at least partially defining a sensing surface. The interface pressure sensor system includes at least a substrate, a first encapsulated sensor group (with a first array of fluid pressure sensors encapsulated by an encapsulation material) disposed on the substrate and a second encapsulated sensor group (with a second array of fluid pressure sensors encapsulated by the encapsulation material) disposed on the substrate and separated from the first encapsulated sensor group by a distance (or pitch).

In these constructions, the electronic device further includes processor operably coupled to the first encapsulated sensor group and the second encapsulated sensor group and configured to: receive, as a first input, output from the first encapsulated sensor group, the first input with a first set of samples defining a first pressure wave; receive, as a second input, output from the second encapsulated sensor group, the second input with a second set of samples defining a second pressure wave; and determine, based on the first pressure wave and the second pressure wave, a health parameter (a heartbeat rate or state, a systolic blood pressure, a diastolic blood pressure, an augmentation index, an arterial state, an arterial disease state, and a sleep state, a respiration state or rate, and so on) of the user.

Related and additional embodiments include a configuration in which the processor is configured to determine a phase offset between the first pressure wave and the second pressure wave. In other or similar cases, the processor may be configured to determine a pulse wave velocity based on a difference between the first pressure wave and the second pressure wave.

Related and additional embodiments include a configuration in which the first array of fluid pressure sensors is arranged in a rhombic pattern so as to separate each fluid pressure sensor by a minimum pitch. As one example, a selected pitch may be on the order of 1 mm, 2 mm or 5 mm. Other pitch separations may be appropriate or preferred in other configurations.

Additional embodiments described herein take the form of a biometric sensor system for an electronic device. The biometric sensor system includes a substrate, a linear array of encapsulated fluid pressure sensor groups disposed along a length of the substrate, and a processor operably coupled to the linear array of encapsulated fluid pressure sensor groups and configured to: receive, as input, a set of samples defining a pressure waveform received by at least one fluid pressure sensor of the linear array of encapsulated fluid pressure sensors; and provide, as output, a health parameter value derived from the set of samples.

Related and additional embodiments include a configuration in which the substrate includes a first portion and a second portion. In this example, the linear array of encapsulated fluid pressure sensor groups may be disposed on the first portion of the substrate. In addition, the biometric sensor system can include a second linear array of encapsulated fluid pressure sensor groups disposed on the second portion, parallel to and offset from the first linear array of encapsulated pressure sensor groups. In these architectures, the set of samples received as input by the process or may be received by at least one fluid pressure sensor of the first linear array of encapsulated pressure sensors or the second linear array of encapsulated pressure sensors.

Some embodiments described herein contemplate leveraging an interface pressure sensor system to receive user input.

For example, some embodiments described herein take the form of an electronic device including at least an enclosure defining an interior surface and an exterior surface opposite the interior surface. The electronic device can include an interface pressure sensor system at least partially coupled to the interior surface and including an outer shear wall defining a module volume and an array of pressure sensor modules within the module volume. Each pressure sensor module of the array includes at least an inner shear wall defining a sensor volume, a fluid pressure sensor disposed within the sensor volume, and an infill encapsulating (e.g., a selected durometer polymer) the fluid pressure sensor within the sensor volume. In many examples, a second encapsulation can be used to encapsulate the array of pressure sensor modules within the module volume (e.g., the second encapsulation can fill the module volume, thereby enclosing the individual pressure sensor modules within the outer shear wall).

Related and additional embodiments may include with a processor operably coupled to the interface pressure sensor system and configured to receive, as input, an output of the interface pressure sensor system that corresponds to a pressure or force applied to the exterior surface of the enclosure. The input can be leveraged to perform a task, to interrupt a process, or for any other suitable hardware, software, or user interface or user interaction purpose.

Related and additional embodiments include a configuration in which the array of pressure sensor modules may be arranged in a linear or rhombic pattern within the outer shear wall.

Some embodiments may include a processor operably coupled to the interface pressure sensor system and configured to receive, as input, an output of the interface pressure sensor system that corresponds to a pressure applied to the exterior surface of the enclosure and, in response, perform one or more operations of a group consisting of: determine a health parameter of a user of the electronic device; and signal a user input may be received.

Additional embodiments described herein take the form of a portable electronic device including at least an interface pressure sensor system including at least: an outer shear wall; a set of pressure modules (each including at least an inner shear wall defining an interior volume and a fluid pressure sensor within the interior volume); and an encapsulation infill encapsulating each pressure module within the outer shear wall and each respective fluid pressure sensor within each respective inner shear wall. In these examples, as with other described examples, the encapsulation infill can define at least a portion of an exterior surface of the portable electronic device that is configured to receive a pressure or force input from a user of the portable electronic device.

Related and additional embodiments include a configuration in which the interface pressure sensor system may be a first interface pressure sensor system, and the portable electronic device includes an array of interface pressure sensor systems arranged in a pattern, the array of interface pressure sensor systems with the first interface pressure sensor system.

Still further embodiments described herein take the form of a pressure input sensor for an electronic device. The pressure input sensor includes a shear wall defining a volume, a fluid pressure sensor disposed within the shear wall, an application specific integrated circuit conductively coupled to the fluid pressure sensor and configured to sample an electrical property of the fluid pressure sensor (the electrical property corresponding to a magnitude of pressure applied normal to the fluid pressure sensor), and an encapsulation infill enclosing the fluid pressure sensor and the application specific integrated circuit within the volume.

These foregoing examples are not exhaustive. It may be appreciated that the foregoing example embodiments, and the various alternatives thereof and variations thereto, are presented, generally, for purposes of explanation and introduction, and to facilitate an understanding of various configurations, architectures, and constructions of a system, such as described below and as illustrated in the accompanying figures.

BRIEF DESCRIPTION OF THE DRAWINGS

Reference will now be made to representative embodiments illustrated in the accompanying figures. It should be understood that the following descriptions are not intended to limit this disclosure to one included embodiment. To the contrary, the disclosure provided herein is intended to cover alternatives, modifications, and equivalents as may be included within the spirit and scope of the described embodiments, and as defined by the appended claims.

The use of the same or similar reference numerals in different figures indicates similar, related, or identical items.

Figure 1A:
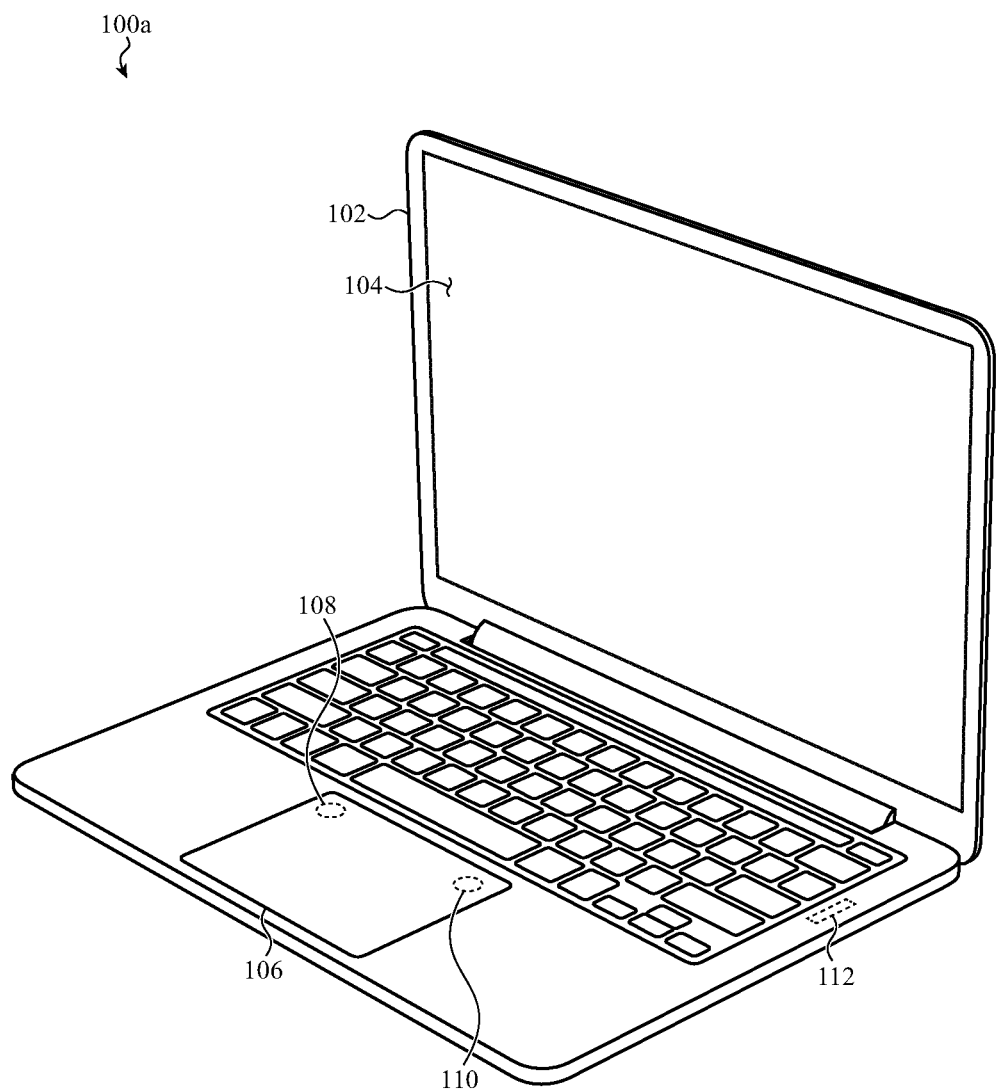
FIGS. 1A-1F depict example electronic devices that can include one or more interface pressure sensor systems, such as described herein.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Embodiments described herein relate to pressure sensing and force sensing in electronic devices. A sensing system as described herein can be incorporated into any suitable electronic device, including portable and stationary electronic devices, medical and consumer electronic devices, industrial devices, and so on.

Example portable consumer electronic devices that can include a sensing system as described herein can include, but may not be limited to: desktop computers; laptop computers; accessory devices (e.g., headphone devices, earbud devices, wearable devices, smart watches, smart cuffs, smart glasses, and so on); peripheral devices (e.g., stylus devices, keyboards, mice, trackpads, and so on); personal medical devices (e.g., at-home health monitors, wearable medical devices, sleep tracking devices, activity tracking devices, and so on); and so on. Example stationary and/or industrial electronic devices include, but are not limited to: medical diagnostic equipment (e.g., radial artery applanation tonometers, sphygmometers, and so on); contour gauges; pressure gauges; scales; and so on.

These foregoing examples are not exhaustive of the types of electronic devices that can incorporate a sensing system as described herein; any suitable electronic device or component can incorporate a sensing system as described herein. In some examples, a sensing system or a portion thereof can be manufactured as a surface mount or other small form-factor component that, in turn, can be seated in any suitable manner, on any suitable substrate, associated with any electrical circuit defining an operation of any suitable electronic device. For simplicity of description the following embodiments reference a configuration in which a sensor or sensing system as described herein is incorporated into a portable consumer electronic device (e.g., laptop device, tablet device, cellular phone, wearable device, personal medical device, accessory device, and so on). It is appreciated that this is merely one example and that other configurations and architectures are possible.

As used herein the phrase "force sensing" and related terminology (and associated structure) refers to operations that can be configured to return a value, whether scalar, analog, or otherwise, corresponding to a measurement convertible to Newtons. Similarly, as used herein the phrase "pressure sensing" and related terminology (and associated structure) refers to operations that can be configured to return a value corresponding to a measurement in Newtons per meter squared (i.e., Pascal).

In this manner, a force sensor, as described herein, can be configured or calibrated to measure pressure by dividing a force measurement obtained as output from the force sensor by a surface area of a sensing surface of the force sensor. Similarly, a pressure sensor, as described herein, can be configured to measure force by multiplying a pressure measurement obtained as output form the pressure sensor by a surface area of the sensing surface of the pressure sensor. In other cases, as noted above, a sensor can be calibrated to output values that correspond to pressure without requiring an area-based or force-based calculation or determination. For example, a force sensor may be calibrated in the field or factory by applying known pressures to that force sensor.

Output from the force sensor during this calibration may be recorded and correlated to the known applied pressure (e.g., stored in a look-up table or other memory structure). In these configurations, a force sensor as described herein may be configured to output value(s) corresponding to, or convertible to, a measurement in Newtons per meter squared.

In further configurations, a sensor as described herein can be configured to output both pressure applied and force applied and/or may be configured to selectable output one or the other. In this manner, it may be appreciated that force sensors referenced herein can be likewise configured to exclusively or additionally output pressure measurements and pressure sensors referenced herein can likewise be configured to exclusively or additionally output force measurements.

Further, it may be appreciated that a sensor or sensing system as described herein can be configured to provide digital and/or analog output. For example, in some embodiments, a digital value may be output from a digital interface associated with a sensor as described herein. The digital value can be provided as input to another system or processor in a series or parallel manner; it can be communicated according to any suitable protocol.

In other configurations, a sensor or sensing system as described herein can be configured to provide analog output. For example, an analog voltage or current magnitude may be output from an analog interface associated with a sensor as described herein. In these constructions, a change in output current or voltage may be proportionally related to a corresponding change in pressure or force detected and/or otherwise received by the sensor.

In yet other examples, a sensor or sensing system as described herein can be configured to provide frequency domain and/or periodic output having one or more properties that correspond to a pressure or force detected or otherwise received by that sensor or sensing system. For example, in one construction, a sensor as described herein can be configured to provide a variable frequency output.

These foregoing examples are not exhaustive; it may be appreciated by a person of skill in the art that a system as described herein, which can include one sensor or more than one sensor, can be configure to provide any suitable digital/discrete domain, analog domain, or frequency domain output that, in turn, corresponds according to a known relationship to a magnitude of force and/or pressure received at a sensing surface of that system at a given time.

As such, for simplicity of description and illustration, the embodiments that follow reference sensors and systems configured to provide digital output. The digital output can have any suitable resolution (e.g., bit length) and may be provided at any suitable sampling frequency. In many examples, as may be appreciated by a person of skill in the art, a sensor or sensing system as described herein can be configured to be sampled at a sampling rate at least twice the highest frequency inflection point if waveforms output from that sensor or system.

More specifically, it may be appreciated that sensors and systems described herein may be preferably sampled at or above an appropriately-selected Nyquist frequency. In other cases, sampling frequency may change and/or may be adjusted in real time. For simplicity of description, sampling frequencies of various embodiments are not referenced below; it may be presumed that an appropriate sampling frequency (which may be static and/or may change) for a given embodiment may be selected.

In this manner, sensors and systems described herein can be leveraged to obtain on-demand force or pressure measurements and/or may be leveraged to provide sets of samples of force or pressure measurements, each of which correspond to a respective sampling time. More simply, a sensor or sensing system as described herein can be configured to provide force/pressure information as a single output (a "sample") and/or may be configured to provide force/pressure information over time (a "waveform").

Accordingly, in view of the foregoing, the example embodiments that follow reference sensors and systems, configured to provide digital output that corresponds to pressure and/or force samples or waveforms, incorporated into portable consumer electronic devices.

Such embodiments reference sensor systems configured to accurately and precisely measure pressure applied at an interface surface of those sensor systems, referred to herein as a "sensing surface." By sampling a sensor system, as described herein, at a sampling rate over a period of time, pressure waveforms characterizing pressure changes at the sensing surface can be obtained.

Certain embodiments described herein can be configured to leverage sets of pressure samples (e.g., pressure waveforms) to determine one or more properties of an object engaged with the sensing surface. For example, in one embodiment, an electronic device incorporating a sensor system as described herein can be used to obtain a blood pressure measurement by placing the sensing surface of the sensor system in contact with a patient's skin above a region of an artery of that patient (e.g., carotid, radial, brachial, and so on). The patient's cardiac cycle induces a palpable pressure wave that can be detected at the sensing surface as a change in pressure over time.

By sampling output of the sensor system of the preceding example at an appropriate sampling rate (e.g., which may be at, or above, a Nyquist rate associated with an average or user-specific cardiac cycle), a pressure waveform corresponding to the patient's cardiac cycle can be obtained and analyzed to determine, estimate, calculate, or otherwise produce one or more values or waveforms corresponding to a one or more cardiac health parameters of the patient. Examples include, but may not be limited to: systolic blood pressure; diastolic blood pressure; pulse wave velocity; pulse transit time; augmentation index; stress state; respiration state; arterial disease state; and so on. These and other examples are discussed in greater detail with reference to certain embodiments described below.

In other cases, a sensing system as described herein can be incorporated into a device configured to monitor a patient's sleep patterns. In such examples, the sensing system can be integrated into a pad, mat, or other insert configured to nest below a mattress. As with the foregoing example, by sampling output of the sensor system at an appropriate sampling rate, a pressure waveform corresponding to the patient's movement, respiration, and/or heart rate can be obtained and analyzed to determine, estimate, calculate, or otherwise produce one or more values or waveforms corresponding to a one or more sleep cycle parameters of the patient. Examples include, but may not be limited to: hypnogram data; respiration rate; sleep state; heart rate; and so on.

In yet further embodiments, a sensing system as described herein can be incorporated into an electronic device configured to receive user input. In such examples, the sensing system can be coupled to a component or surface of the electronic device such that a user of that electronic device can provide input by pressing or applying a force input to the component or surface. For example, a sensing system as described herein can be positioned below a display of a portable electronic device. As a result of this construction, a user of the electronic device can apply a force to the display which, in turn, can be received as a user input. In response to receiving the user input, the portable electronic device can perform a function, interrupt a process, or perform any other suitable task or operation.

In view of the foregoing examples, it may be appreciated that a sensing system as described herein can be incorporated into a number of electronic devices in a number of ways for a number of purposes. In other words, these foregoing examples are not exhaustive. It may be appreciated that a sensing system as described herein can be leveraged in a number of suitable ways.

A sensing system as described here can be referred to as an "interface pressure sensor system." An interface pressure sensor system can be implemented as a collection of one or more individual pressure sensitive elements referred to as "pressure sensor modules."

A pressure sensor module includes a single pressure-sensitive structure (and optionally associated circuitry or electronics to obtain samples therefrom or thereof) packaged as a surface mount component. More specifically, the pressure sensor module includes a rigid module enclosure coupled to a rigid substrate. Together, these components define an open interior volume into which a microelectromechanical fluid pressure sensor, such as a barometer, can be disposed. The open interior volume can thereafter be potted, encapsulated, or otherwise filled with an encapsulation material (e.g., polymer, thermoset plastics, polyimide, silica, silicone, resins, epoxies, and so on). The encapsulation material, once cured, defines an interface referred to as a sensing surface that can receive pressure or force as an input.

The above-described construction confers many benefits. In particular, the rigid module enclosure serves as a shear wall that redirects shear forces and shear pressures away from the sensing surface defined by the encapsulation material and imparted to the fluid pressure sensor. In another, more simple and non-limiting, phrasing, the shear wall of embodiments of pressure sensor modules as described herein concentrates the sensitivity of the fluid pressure sensor along a single direction, substantially normal to the sensing surface defined by the encapsulation material. In this manner, any normal force or pressure applied to the sensing surface is transferred, via the encapsulation material, directly to the fluid pressure sensor.

Many embodiments described herein reference an example pressure sensor as a microelectromechanical fluid pressure sensor, but it may be appreciated that this is merely one example. In other cases, other micro or macro electromechanical pressure sensor topologies may be used. However, in many embodiments, a fluid pressure sensor such as a barometer may be selected for its exceptionally high sensitivity to small changes in pressure. In some cases, an off-the-shelf fluid pressure sensor can be selected as the pressure sensor of a pressure sensor module, as described herein. In such examples, the fluid pressure sensor may be relieved from its module enclosure or protective outer cover prior to disposing that sensor within a volume defined by a shear wall, as described above.

Regardless of configuration, it may be appreciated that a pressure sensor module as described herein includes a shear wall and an encapsulated fluid pressure sensor within a volume defined by that shear wall. As a result of this construction, a pressure sensor module can be manufactured as a surface-mount component having a small form factor (e.g., on the order of one square millimeter) that is exceptionally sensitive to changes in pressure applied normal or substantially normal to a sensing surface, defined by an outer surface of the encapsulation material, of the pressure sensor module.

A pressure sensor module, as described above, can be communicably and/or conductively coupled to any suitable circuit or system and may be configured to provide output to that circuit or system, which, in turn can receive the output as input to perform a task.

As may be appreciated, a pressure sensor module as described herein is a small form-factor electronic component that can be used with other pressure sensor modules. For example, in one embodiment, a grid or array of pressure sensor modules can be disposed onto a substrate and separated by a particular pitch. In this example, each pressure sensor module can serve as a single "pixel" of a pressure imaging device.

In another example, multiple pressure sensor modules can be arranged in a linear array. As a result of this construction, the multiple pressure sensors can be used to detect a pressure wave from a source that may be difficult to specifically or precisely locate.

For example, in one embodiment, an interface pressure sensor system as described herein can be used as an applanation tonometer configured to detect or characterize one or more characteristics of a patient's cardiac cycle by placing the interface pressure sensor system over the patient's radial artery. As may be known to persons of skill in the medical data collection art, locating a suitable position for a conventional applanation tonometer directly over the radial artery may be a difficult and time-consuming process, requiring specialized training and patience.

To the contrary, an embodiment as described herein can position multiple different pressure sensor modules in a row which, in turn, can be placed in contact with a skin surface at the interior of the patient's wrist; a length of the linear arrangement of pressure sensor modules may extend generally perpendicular to the radial artery.

In particular, as a result of the linear arrangement of pressure sensor modules in this embodiment, it may be appreciated that at least one pressure sensor module of the linear array may be positioned directly over the patient's radial artery and may, thereafter, be selected to sample a pressure wave that corresponds to the patient's cardiac cycle. In these embodiments, it may be readily appreciated that an array or pattern of individual pressure sensors can substantially improve misplacement tolerance over conventional systems, thereby enabling an interface pressure sensor system as described herein to be used by any individual, whether trained or otherwise, to obtain important medical diagnostic information from a patient. In some examples, the patient may be able to suitably place the interface pressure sensor system of the patient's own radial artery, enabling at-home non-invasive blood pressure monitoring.

Still further embodiments can be configured in ways that further improve positional independence of sensing systems as described herein. For example, in some embodiments, a linear array of pressure sensor modules, as described herein, can be accompanied by a second linear array of pressure sensor modules, offset from the first array of pressure sensor modules by a particular selected pitch. In this manner, the two linear arrays form a repeating rhombic pattern that extends for a distance. In this construction, the pitch separating each pressure sensor module may define the linear positional sensitivity of the interface pressure sensor system itself. For example, if no sensor of the first array of pressure sensor modules is sufficiently aligned with a pressure source (e.g., a radial artery), at least one pressure sensor module of the second array may be aligned with the pressure source. Further embodiments, can include additional offset pressure sensor modules.

More broadly, in view of the foregoing it may be appreciated that in some implementations, multiple pressure sensor modules can be grouped together into "sensor groups" that can be cooperatively operated to measure pressure over a larger area than individual pressure sensor modules can measure independently.

In certain constructions of the foregoing example, some sensor groups can be disposed together into a single macro-module enclosure that defines a second, outer, shear wall that, in turn, can be filled with an infill material, encapsulation material, potting material, and the like. In these examples, a second layer of shear force protection can be afforded to each individual module circumscribed by the second shear wall.

More generally, in some embodiments, multiple individual pressure sensor modules can be grouped together and encapsulated together within a larger, common, shear wall. Phrased in another manner, certain constructions of interface pressure sensor systems as described herein include an outer shear wall (also referred to as an outer enclosure, outer module enclosure, outer ring, perimeter sidewall, and so on) that circumscribes an array or individual pressure sensor modules. The individual pressure sensor modules of an encapsulated group can be disposed in any suitable pattern in any suitable number. For simplicity of description, many embodiments that follow reference sensor groups that include four individual pressure sensor modules disposed in a rhombic (or diamond) pattern, separate by a selected pitch. Phrased in another manner, an example sensor group as described herein can include two rows of individual pressure sensor modules, each row containing two individual pressure sensor modules. The first row of pressure sensor modules can be offset relative to the second row of pressure sensor modules. As a result of this pattern, the sensor group can cooperate to define a larger-area sensing surface that individual pressure sensor modules themselves define.

In still further embodiments an array of groups of sensors can be used. For example, groups of sensors can be arranged in a linear pattern. In this example as with preceding examples, each group can include four individual pressure sensors. As a result of these constructions, an interface pressure sensor system can efficiently sense pressure waves across a wide area, or a wide length.

The foregoing architectures are not exhaustive of the various layouts and configurations of an interface pressure sensor system as described herein. For example, in some embodiments, only a single pressure sensor module may be required. In other cases, only a single group of pressure sensor modules (encapsulated together within a macro-module shear wall) may be required. In other cases, an array of groups of pressure sensor modules may be required. Any suitable configuration may be provided.

In any of the foregoing or following described embodiments/implementations, it may be appreciated that two or more pressure sensor modules may be operably coupled to facilitate differential sensing.

These foregoing and other embodiments are discussed below with reference to FIGS. 1A-14. However, those skilled in the art will readily appreciate that the detailed description given herein with respect to these figures is for explanation only and should not be construed as limiting.

Generally and broadly, FIGS. 1A-1F and FIG. 2 depict example electronic devices that can incorporate an interface pressure sensor system as described herein. As noted above, the interface pressure sensor system can include one or more arrays of one or more encapsulated groups of one or more individual pressure sensor modules. An individual pressure sensor module, as noted above, is typically implemented with a microelectromechanical fluid pressure sensor disposed and encapsulated within an interior volume of a rigid module enclosure referred to herein as a shear wall. The shear wall and the encapsulation material cooperate to protect the fluid pressure sensor and to concentrate pressures and forces received by the module along a normal direction to the fluid pressure sensor. As a result of this construction, a fluid pressure sensor—which may already be configured for high sensitivity and high precision pressure detection—can be further improved by mechanically directing input pressure along a single sensing axis, namely, a normal to a sensing surface defined by the encapsulation material itself.

In these embodiments, an interface pressure sensor system can be used to detect, with high accuracy and precision, either or both pressure applied to a sensing surface and/or force applied to the sensing surface. In view of this, it may be appreciated that an interface pressure sensor system as described herein can be implemented with any suitable number of arrays, any suitable number of groups (whether encapsulated groups or non-encapsulated groups), and/or with any suitable number of individual pressure sensor modules. Similarly, it may be appreciated that an interface pressure sensor system as described herein can be incorporated into a number of suitable electronic devices, some of which are described in reference to FIGS. 1A-1F. For example, an interface pressure sensor system can be incorporated into portable consumer electronic devices to, in some implementations, received force or pressure input. In other cases, an interface pressure sensor system can be incorporated into a portable medical device, such as an applanation tonometer or other appliance configured to detect or quantify blood pressure of a patient by applanation of an artery and pressure wave analysis thereof, such as the patient's radial artery. For example, pulse transit time may be calculated and correlated (proportionately) to blood pressure. In yet other examples, an interface pressure sensor system can be used to detect fluid pressure or mechanical pressure in an environment where an environment-exposed barometric or other pressure sensor would not be suitable.

The foregoing example embodiments are not exhaustive; it may be appreciated that an interface pressure sensor system can be integrated into and/or otherwise leveraged by any number of suitable electronic devices.

Similarly, in some implementations, a single electronic device can include multiple discrete interface pressure sensor systems, which may be configured in the same or a different manner.

For example, in some cases, an electronic device can be a wearable electronic device configured to be worn by a user on the wrist. In this example, the electronic device can include a first interface pressure sensor system to receive user input to a display of the wearable electronic device. In this configuration, at least a portion of the first interface pressure sensor system can be mechanically coupled (either directly or indirectly, such as by one or more linkages or couplings) to the display of the wearable electronic device. As a result of this construction, when a user/wearer of the electronic device applies a force to the display by pressing, the first interface pressure sensor system can receive that force and characterize the same, signaling that a user input has been received if one or more characteristics of the received force input satisfy a parameter to classify the force as an intentional user input.

For example, in one implementation, the parameter may be a threshold. In such constructions, the wearable electronic device or, more specifically, the first interface pressure sensor system, can be configured to signal that a user force or pressure input has been received if and only if a magnitude of the force received (detected by the first interface pressure sensor system) satisfies the threshold. In other cases, the interface pressure sensor system can include and/or can be coupled to a classifier configured to detect and/or label one or more force input gestures, such as a double or triple "click" application of force. In such constructions, the classifier can be configured to label a force/pressure waveform received by the first interface pressure sensor system as a force-gesture input if and only if one or more inflection points of a pressure waveform received by the first interface pressure sensor system matches a profile associated with that label. More generally and broadly, it may be appreciated that the foregoing examples that leverage a sample and/or waveform output of the first interface pressure sensor system to signal user input are not exhaustive; it is appreciated that an interface pressure sensor system such as the first interface pressure sensor system described in reference to the foregoing example is not exhaustive. More broadly, it is appreciated that in some examples, an electronic device can leverage an interface pressure sensor system as an input sensor.

Continuing the preceding example, the wearable electronic device can include a second interface pressure sensor system. The second interface pressure sensor system can be configured to detect one or more health parameters of a user/wearer of the electronic device. For example, the second interface pressure sensor system may be disposed to defined a sensing surface that contacts an interior region of the user/wearer's wrist, generally positioned over the user/wearer's radial artery. As a result of this arrangement, the second interface pressure sensor system can be configured to detect pressure waves expanding and contracting the user's skin that result from the user's cardiac cycle. Samples and/or waveforms output from the second interface pressure sensor system can be used to obtain, without limitation: heart rate; blood pressure; augmentation index; arterial age (e.g., as compared against chronological age); pulse wave velocity; stress state; and so on. Each of these parameters can independently inform one or more health data of the user, which in turn can be presented to the user/wearer, a medical professional, and/or a designated emergency contact of the user/wearer. For example, if an output of the second interface pressure sensor system corresponds to a sudden drop in blood pressure, it may be determined that the user/wearer has fainted. This determination may be supported with output from one or more other sensors of the wearable electronic device, such as an accelerometer configured to monitor for falls. Once the wearable electronic device, leveraging outputs from the second interface pressure sensor system and/or another sensor or sensing system, determines that the user/wearer has fainted, emergency personnel and/or emergency contacts can be automatically contacted.

In other cases, other health recommendations can be made to a user/wearer based on blood pressure or stressor information. For example, the wearable electronic device may be configured to remind the user/wearer to take a deep breath and/or to take other stress-reducing interventional steps (e.g., meditation, taking a break from a stress-inducing activity, and so on). In yet other examples, the wearable electronic device can track blood pressure regularly over the course of days or weeks to determine patterns. Deviation from these patterns may result in notifications or reminders, such as reminders to be active, reminders to take prescription medication, and so on.

In yet further embodiments, a force sensor, pressure sensor, or more generally a module as described herein can be leveraged for a purpose other than force/pressure input sensing. For example, in some cases, sensors and sensor modules as described herein can be configured for acoustic sensing (subsonic, sonic, and/or ultrasonic ranges) or ambient pressure (barometric) sensing.

These foregoing example use cases are not exhaustive; it may be appreciated generally and broadly that an interface pressure sensor system can be used for a number of suitable purposes, such as to receive input, to monitor one or more health parameters, or combinations thereof. Use cases vary from embodiment to embodiment and implementation to implementation.

FIGS. 1A-1F depict example electronic devices that can include one or more interface pressure sensor systems, such as described herein.

In particular, FIG. 1A depicts an electronic device 100a. The electronic device 100a in this example is implemented as a laptop computer. The electronic device 100a includes an upper clamshell portion and a lower clamshell portion, coupled at a hinge. The upper portion and the lower portion cooperate to define a housing 102 that encloses and supports internal and operational components of the electronic device 100a. The housing can be formed from any suitable material, including metals, glass, plastics, ceramics, organic materials, and the like or combinations thereof.

The housing 102 of the electronic device 100a encloses a display 104 that can be used to generate a graphical user interface to provide visual information to a user of the electronic device 100a and to solicit and receive input from that user. More specifically, the display 104 of the electronic device 100a can be configured to render, or otherwise depict, one or more graphical user interfaces, in turn defined by one or more instances of software executing as a result of an operation of a processor of the electronic device 100a.

In this manner, more generally, the housing 102 of the electronic device 100a can define one or more interior volumes that enclose, support, and/or otherwise protect one or more operational or functional components not depicted in FIG. 1A, for simplicity of illustration. Such example components can include, but are not limited to: processors; memory (whether persistent or working memory); sensors; input devices; output devices; haptic devices; audio/acoustic devices; imaging devices; power supplies (e.g., batteries); input/output ports; wireless communications modules; and so on. Other electronic device can include different, additional, or alternative internal components.

In typical configurations, a processor of the electronic device 100a can be configured to access a persistent memory of the electronic device 100a in order to obtain one or more executable binary files or other program code (collectively, herein, application or program "assets"). At least a portion of the obtained assets can be thereafter loaded into a working memory to at least partially instantiate an instance of a particular software application. The software application can execute over an operating system, and/or may be containerized or virtualized, so as to execute over bare metal. A person of skill in the art may readily appreciate that many suitable techniques of instantiating software may be leveraged.

Once a software application is instantiated over the electronic device 100a, that software application may be configured to render a graphical user interface, as noted above.

The graphical user interface can be configured to display one or more graphical user interface elements and/or affordances on the display. These elements and/or affordances can be used by the software application instance to provide information to and/or solicit and receive information/input from a user of the electronic device 100a.

As noted above, the housing 102 of the electronic device 100a can enclose a number of sensors and/or user input devices that can be leveraged by a user of the electronic device 100a to provide input to the graphical user interface and/or, more generally, to provide input to any given instance of software executing over the electronic device 100a. Example input devices include, but are not limited to: cameras; microphones; trackpads; mice; stylus devices; depth sensors; time of flight sensors; force input systems; touch input systems; keyboards; and so on or any combination thereof.

For example, in the illustrated embodiment, the electronic device 100a includes a trackpad 106. The trackpad 106 can be implemented with any suitable position-tracking technology (e.g., capacitive, resistive, inductive, and so on) that can be leveraged to determine a position, either relative or absolute, of a user's finger (or fingers) engaging an outer sensing surface of the trackpad 106. The trackpad 106 may be a single touch or multi-touch trackpad. In typical implementations, the trackpad 106 includes an array of capacitive sensors configured for mutual and/or self-capacitive operation. In this manner, and as a result of this construction, the trackpad 106 can readily determine an input location (or multiple input locations) of a user's finger once the user touches the trackpad.

As may be known to a person of skill in the art, a capacitive touch input sensor, such as in the above-referenced example construction of the trackpad 106, may not be readily suitable for detect force or pressure input. In other words, conventional trackpad technologies may be best suited for position detection but may not be particularly suited to detect force applied at that position (or positions, in the case of a multi-touch trackpad implementation of the trackpad 106).

To that end, the electronic device 100a can further include an interface pressure sensor system as described herein. In the illustrated embodiment, the electronic device 100a includes a first interface pressure sensor system configured to detect force input to the trackpad 106 and a second interface pressure sensor system configured to detect force input to an edge of the housing 102.

In particular, the first interface pressure sensor system can include two separate pressure sensor modules, and/or two separate groups, thereof (such as described above). A first pressure sensor module group 108 and a second pressure sensor module group 110 can be positioned below the trackpad 106. More specifically, one or more sensing surface of the first pressure sensor module group 108 and the second pressure sensor module group 110 can be adhered to and/or otherwise mechanically coupled to an interior surface of the trackpad 106. As a result of this construction, a force input received to the trackpad 106 can be imparted to at least one pressure sensor module of either, or both, the first pressure sensor module group 108 or the second pressure sensor module group 110.

The second interface pressure sensor system of the electronic device 100a can be disposed along an edge of the lower portion of the housing 102. As with the first, the second interface a pressure sensor system of the electronic device 100 can include one or more individual pressure sensor modules, arranged in a group. In the illustrated embodiment, the second interface pressures sensor system includes a third pressure sensor module group 112. In this example, the third pressure sensor module group 112 can include multiple individual pressure sensor modules arranged in a linear array. As a result of this arrangement, a user of the electronic device 100a can slide the user's finger along a length of the third pressure sensor module group 112 in order to provide input to the electronic device 100a. For example, as a result of this construction, different pressure sensor modules of the third pressure sensor module group 112 can detect different amounts of pressure at different times, generally corresponding to a magnitude of force/pressure applied by the user to the housing 102 and corresponding to a location of the application of that force/pressure. In one example, output from the third pressure sensor module group 112 can be used to adjust a brightness or a volume of the electronic device. In other examples, output(s) from the third pressure sensor module group 112 can be leveraged for a different purpose.

In this manner, the third pressure sensor module group 112 can be used as a linear input device configured to sense user input through an otherwise rigid housing portion.

Although the embodiment depicted in FIG. 1A contemplates inclusion of interface pressure sensor systems in order to receive user input, this implementation is merely one example. For example, in some embodiments, one or more of the interface pressure sensor systems of FIG. 1A can be leveraged for health, biometric, or medical sensing as well, or as an alternative. For example, the first interface pressure sensor system may be configured to detect a heartrate of a user providing input to the trackpad 106 (e.g., by monitoring for low-frequency periodic pressure wave that generally corresponds to a human cardiac cycle).

As a result of this construction, the trackpad 106 can more effectively reject non-human input and/or may be able to provide rich feedback to user (e.g., to provide health suggestions or notifications) and/or may be able to determine a stressor state of the user. For example, if the electronic device 100a is used to instantiate an instance of a video game, the user's heartrate detected by the first interface pressure sensor system (while the user leverages the trackpad 106 to provide input to the game), may be used to inform an operation of the video game itself.

For example, a raised heartrate may be leveraged by the game to reduce occurrences of stress-inducing imagery. In another example, a lowered heartrate may cause the game to offer an incentive or sidequest to the player to maintain engagement. In yet another example, the player's heart rate may be provided as input to a parental tracking system that can inform a parent of a child's engagement with the video game. In such examples, one or more notifications may be generated to a parent if the child's heart rate exceeds a threshold while playing the video game.

In yet further examples, biometric data obtained by an interface pressure sensor system can be used for other purposes along with user input. For example, a login form rendered by the electronic device 100a may require the user to hold the user's finger on the trackpad for a period of time as a proof of physical presence. In another example, an interface pressure sensor system can be used to determine whether the upper clamshell portion of the housing 102 of the electronic device 100a is in a closed position or an position.

In yet other examples, a pressure sensor module can be used to determine whether a cord or cable is inserted into a particular receptacle. In yet another example, an interface pressure sensor system can be used to determine a stress level of a user operating that electronic device (e.g., monitoring for sharp pressure impacts resulting from a frustrated battering of the electronic device 100a and/or monitoring for increased heart rate, and/or monitoring for increased acoustic noise that can be labeled by a classifier as shouting, and the like). In turn, the user's stress level can be used to inform an operation of the electronic device 100a.

For example, of the user exhibits suddenly elevated stress, the electronic device 100a may execute a routine to determine whether an instance of software has halted or if a background process has begun consuming computational resources that could otherwise be allocated to a front-most application. In such examples, the electronic device 100a can use user stress information, which can be obtained at least in part by receiving as input an output of an interface pressure sensor system as described herein, to overclock a processor, to kill a process, to reallocate computing or memory resources, and so on. In this manner, an interface pressure sensor system as described herein can self-regulate to reduce the overall stress level of a user operating that electronic device which, in turn, can improve the overall health of that user.

These foregoing examples are not exhaustive. It may be appreciated that an interface pressure sensor system as described herein can be simultaneously used for both input sensing and health parameter sensing, and outputs of either operation can be leveraged by an electronic device for any suitable purpose.

Figure 1B:
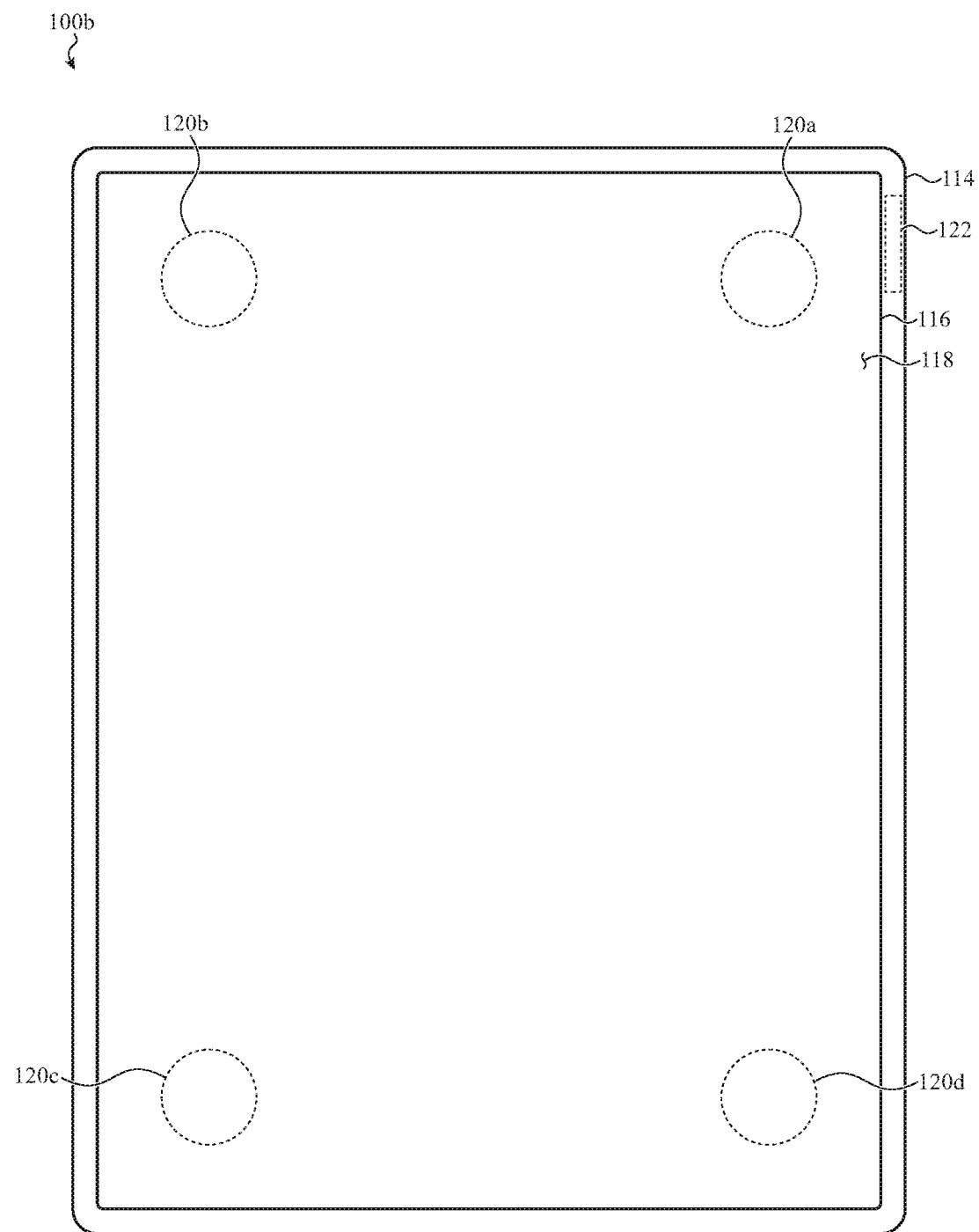

Furthermore, a laptop device is merely one example electronic device that can incorporate an interface pressure sensor system as described herein. For example, FIG. 1B depicts a tablet computing device as an example electronic device, identified as the electronic device 100b. In this example embodiment, the electronic device 100b includes a housing 114 that encloses and supports internal components of the electronic device 100b, including but not limited to: a processor; a working memory; a persistent memory; a user input sensor; a microphone; a speaker; wireless communications systems (e.g., Bluetooth, Wi-Fi, Ultra-Wide Band, optical communications); and so on. The electronic device 100b, as with the preceding example illustrated embodiment, can include a display 116 that can be leveraged to render a graphical user interface 118. One or more graphical user interface elements and/or affordances cooperating to define the graphical user interface 118 can be generated by an instance of software executing over one or more computational resources of the electronic device 100b.

In this example embodiment, an interface pressure sensor system can be used to receive force or pressure input through the display 116. In particular, similar to the preceding illustrated embodiment, a first interface pressure sensor system can include one or more discrete groups (or arrays of groups) of individual pressure sensor modules disposed along a rear surface of the display 116. For example, as illustrated, four separate groups of individual pressure sensor modules are illustrated as the pressure module groups 120a, 120b, 120c, 120d. These four pressure sensor groups can be leveraged to receive user force input, user pressure input, to obtain one or more health parameters, and so on (such as described above).

Additionally, the electronic device 100b can include a second interface pressure sensor system that includes another group (identified as the group of pressure sensor modules 122) of individual pressure sensor modules. The group of pressure sensor modules 122 an be coupled to, and/or positioned adjacent to a sidewall of the housing 114 of the electronic device 100b. In this manner, and as a result of this construction, force input applied to a sidewall region of the housing 114 can be received as a user input to the electronic device 100b.

As with other embodiments described herein, it may be appreciated that the construction and configuration of both the electronic device 100b and the interface pressure sensor systems thereof as illustrated is not exhaustive. In particular, an electronic device can include any suitable number of interface pressure sensor systems as described herein, which in turn can be coupled to, or otherwise integrated with, any suitable surface of that electronic device including, but not limited to: sidewall surface; planar surfaces; curved surfaces; rigid surfaces; flexible surfaces; display surfaces; non-display surfaces; front surfaces; back surfaces; edge surfaces; bezel surfaces; input surfaces; haptic output surfaces; and so on. In addition, it may be appreciated that an interface pressure sensor system can additionally or alternatively be integrated into accessory devices configured to communicably, magnetically, or otherwise mechanically couple to an electronic device including, but not limited to: soft goods (e.g., watch bands, cases, or protective sleeves and so on); peripheral input or output devices (e.g., keyboards, mice, trackpads, stylus devices, headphone devices, earbud devices, eyeglass devices); power transfer devices (e.g., docks, charging mats, charging stands); external displays (e.g., vehicle infotainment systems, secondary monitors, and so on); peripheral cables or dongles; and so on.

Figure 1C:
Figure 1D:
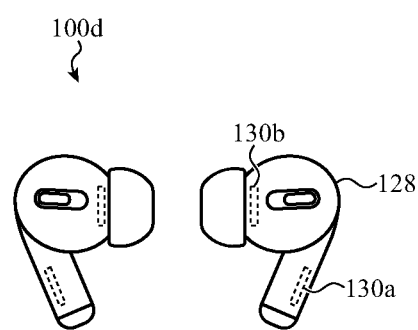

For example, certain peripheral devices are illustrated in FIGS. 1C-1D. In particular, FIG. 1C depicts an electronic device 100c implemented as a smart stylus device. The electronic device 100c can be used to provide input to another electronic device, such as the tablet device as shown in FIG. 1B. As with other electronic devices described herein, the electronic device 100c includes a housing 124 that can enclose, support, and/or otherwise protect: a processor; a memory; a battery; a wireless communications module; in addition to other components, sensors, and systems.

In such example embodiments, the electronic device 100c can incorporate an interface pressure sensor system, as described herein, to receive user input. For example, the interface pressure sensor system can include a first pressure sensor module 126a positioned at an eraser end of the electronic device 100c. The pressure sensor module 126a can be used, in one example, to determine pressure applied by the eraser end to a surface. The interface pressure sensor systems can include a second pressure sensor module 126b disposed within, or adjacent to, a writing end of the stylus that is opposite the eraser end along a length of the housing 124. The second pressure sensor module 126b may be used, in one example, to select or toggle an operating mode of the electronic device 100c or an operating mode of a software application executing on an electronic device to which the electronic device 100c is providing input. For example, by applying pressure to the second pressure sensor module 126b, a user of the electronic device 100c can change between writing colors, writing tip types, and so on.

In other cases, an accessory device can include an interface pressure sensor system in another way. For example, FIG. 1D depicts a pair of wireless earbuds, identified as the electronic device 100d. In this example embodiment, an interface pressure sensor system can be incorporated into a housing 128 of either or both earbuds of the electronic device 100d. In particular, in the illustrated embodiment, the interface pressure sensor system includes a first pressure sensor module 130a and a second pressure sensing module 130b. In this construction, the first pressure sensing module 130a, disposed within an extended portion of the wireless earbud, can be used to receive user input. For example, a user/wearer of the electronic device 100d can squeeze a portion of the housing 128 in order to change an operational mode of the electronic device 100d. For example, to play or pause media played through a speaker of the electronic device 100d, to increase or decrease volume of media played through the speaker, to initiate or terminate ambient noise cancellation, to allow or suppress pass-through sound, to enable or disable a microphone, and so on. In other cases, a squeeze can be received as input to launch a smart assistant and/or to change an operational mode of, or to perform a task (e.g., launching a smart assistant, initiating a telephone call, terminating a telephone call, and so on) by, a second electronic device to which the electronic device 100d is communicably coupled (e.g., cellular phone, media device, television, and so on). In some constructions, the second pressure sensing module 130a may be disposed in a portion or section of the housing 128 configured to rest within or, be in contact with, a skin surface of the user/wearer's ear. In this construction and as a result of this placement, the second pressure sensing module 130a can be used to obtain one or more health parameters of the user/wearer, for example heart rate, respiration rate, or blood pressure.

In view of these foregoing embodiments, it may be appreciated that an interface pressure sensor system can be incorporated into any suitable electronic device (see, e.g., FIGS. 1A-1B) or any suitable accessory to an electronic device (e.g., FIGS. 1C-1D). In still further implementations, an interface pressure sensor system can be incorporated into a wearable health monitor device, such as a smart watch or a sleep monitor.

Figure 1E:
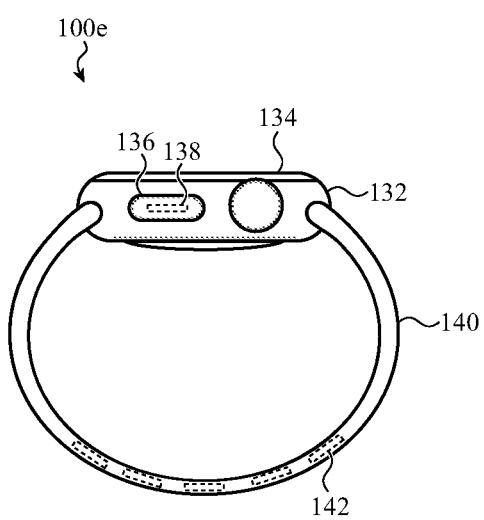

In particular. FIG. 1E depicts a wearable health monitor or, more generally, a wrist-worn wearable electronic device, identified as the electronic device 100e. In this example, as with preceding electronic device embodiments, the electronic device 100e can include a housing 132 that encloses and supports a processor, a memory (either or both persistent/non-volatile and working/volatile) and a display 134. The display 143 can be used to convey information to a user/wearer of the electronic device 100e. In this construction, as with other constructions, an interface pressure sensor system or more than one interface pressure sensor systems can be used to receive user input and/or to characterize or quantify a heath parameter of the user/wearer. For example, in the illustrated embodiment, an input-configured interface pressure sensor system can be disposed, at least partially, within a button 136. More specifically, a pressure sensor module 138 can be disposed within the button 136 in order to determine a pressure/force input applied to the button 136 by a user/wearer of the electronic device 100e.

In addition, the electronic device 100e can include a band 140 configured to removably couple the electronic device 100e, an in particular removably couple the housing 132, to a wrist of a user/wearer. In this embodiment, the band 140 can include an interface pressure sensor system within a body of the band 140. In many embodiments, the interface pressure sensor system is disposed such that a sensing surface of the interface pressure sensor system interfaces/touches an interior surface of the user/wearer's wrist. More particularly, the band 140 can have insert molded therein at least one pressure sensor module or pressure sensor module group 142 that, as a result of the positioning within the band 140 (e.g., at least partially diametrically opposite the housing 132), can be configured to detect pressure waves that result from the user's cardiac cycle. More specifically, the interface pressure sensor system of this example embodiment can be positioned such that at least one pressure sensor module (as described herein) of the interface pressure sensor system is placed in contact with the user/wearer's radial artery. As with preceding embodiments, pressure wave information obtained a result of interfacing a user/wearer's radial artery can be used to determine, without limitation: blood pressure; pulse transit time; augmentation index; arterial age; stressor state; heart rate; pressure wave velocity; and so on.

Figure 1F:
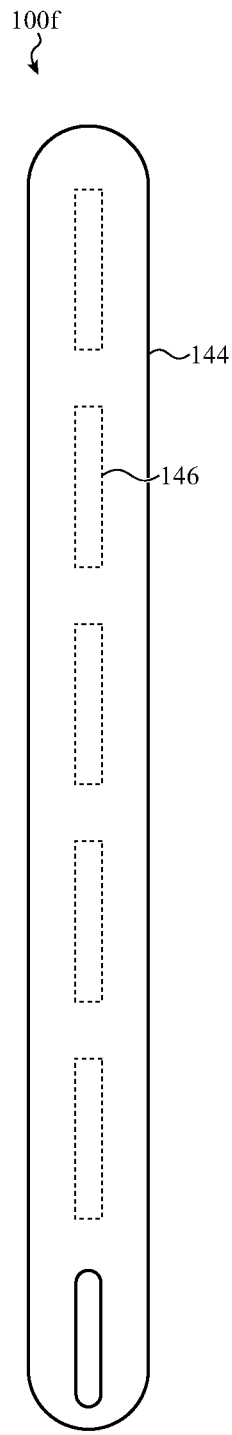

In yet further embodiments, an interface pressure sensor system can be incorporated into a stationary health monitoring device, such as a sleep monitor. FIG. 1F depicts a sleep monitor device configured to be positioned below a sleep surface and configured to measure movement in order to evaluate a sleep state, respiration rate, and/or heart rate of one or more sleeping persons.

In the illustrated embodiment, the sleep monitor device is illustrated as the electronic device 100f. As with other electronic device embodiments described herein, the electronic device 100f includes a housing 144 into which one or more interface pressure sensor systems can be disposed. For simplicity of illustration, a single interface pressure sensor system is identified as the interface pressure sensor system 146.

These foregoing embodiments depicted in FIGS. 1A-1F and the various alternatives thereof and variations thereto are presented, generally, for purposes of explanation, and to facilitate an understanding of various configurations and constructions of a system, such as described herein. However, it will be apparent to one skilled in the art that some of the specific details presented herein may not be required in order to practice a particular described embodiment, or an equivalent thereof.

Thus, it is understood that the foregoing and following descriptions of specific embodiments are presented for the limited purposes of illustration and description. These descriptions are not targeted to be exhaustive or to limit the disclosure to the precise forms recited herein. To the contrary, it will be apparent to one of ordinary skill in the art that many modifications and variations are possible in view of the above teachings.

For example, it may be appreciated that the depicted wearable electronic devices are merely examples and that in other cases, other devices can be configured to be worn or implanted in other portions of a user/wearer's body. Examples include fingers, teeth, forearm, chest, thigh, ankle, back, neck, and so on.

In addition, it may be appreciated that the described electronic devices are not exhaustive of all electronic device types that can incorporate an interface pressure sensor system, such as described herein.

Figure 2:
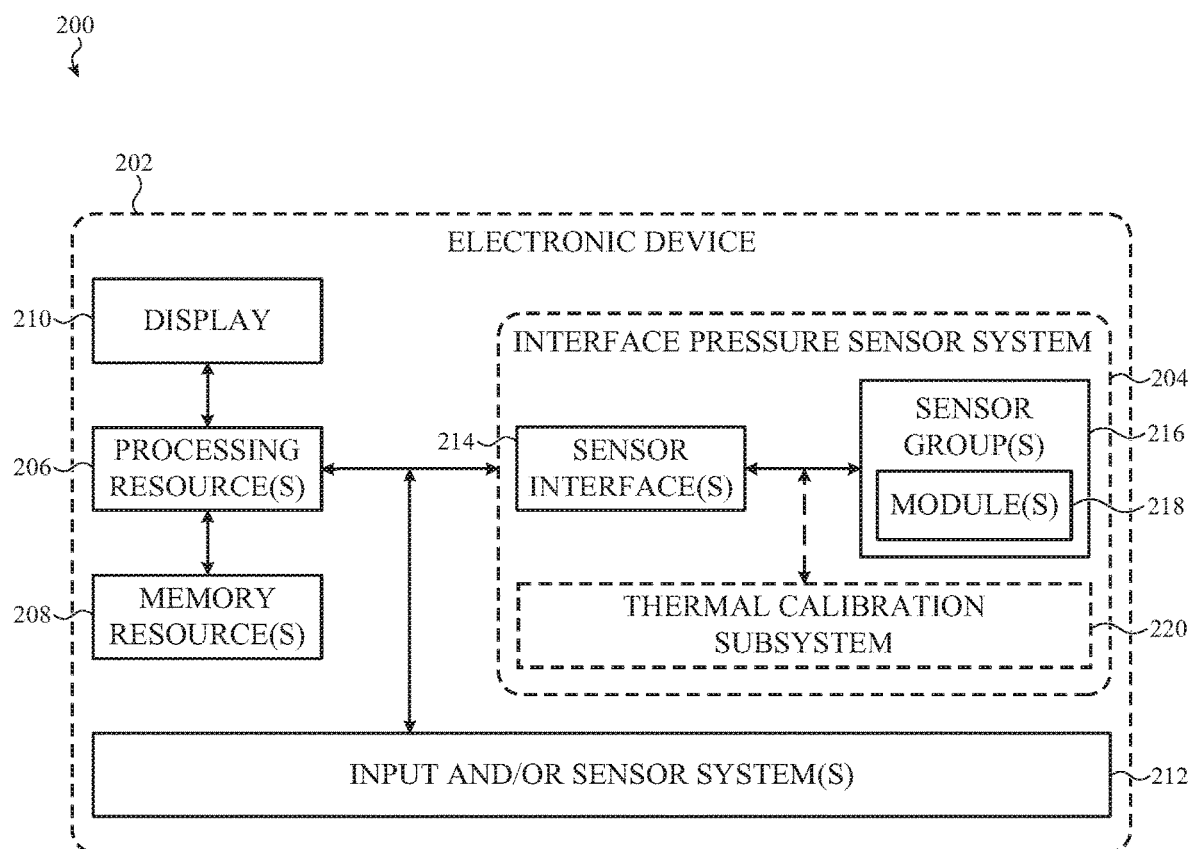
FIG. 2 depicts a system diagram of an example electronic device including an interface pressure sensor system, such as described herein.

For example, more generally and broadly, FIG. 2 depicts a system diagram of an example electronic device including an interface pressure sensor system, such as described herein. This system diagram depicts a simplified representation of an electronic device 20o. The electronic device 200 includes a housing 202 into which an interface pressure sensor system 204 is disposed. The interface pressure sensor system 204 is communicably, conductively, and/or mechanically coupled to a computing or processing resource configured to receive, as input, one or more outputs of the interface pressure sensor system 204. Such outputs may be provided as analog outputs, digital outputs, frequency-domain outputs or any other suitable outputs.

As used herein, the term "computing resource" (along with other similar terms and phrases, including, but not limited to, "computing device" and "computing network")

refers to any physical and/or virtual electronic device or machine component, or set or group of interconnected and/or communicably coupled physical and/or virtual electronic devices or machine components, suitable to execute or cause to be executed one or more arithmetic or logical operations on digital data.

Example computing resources contemplated herein include, but are not limited to: single or multi-core processors; single or multi-thread processors; purpose-configured co-processors (e.g., graphics processing units, motion processing units, sensor processing units, and the like); volatile or non-volatile memory; application-specific integrated circuits; field-programmable gate arrays; input/output devices and systems and components thereof (e.g., keyboards, mice, trackpads, generic human interface devices, video cameras, microphones, speakers, and the like); networking appliances and systems and components thereof (e.g., routers, switches, firewalls, packet shapers, content filters, network interface controllers or cards, access points, modems, and the like); embedded devices and systems and components thereof (e.g., system(s)-on-chip, Internet-of-Things devices, and the like); industrial control or automation devices and systems and components thereof (e.g., programmable logic controllers, programmable relays, supervisory control and data acquisition controllers, discrete controllers, and the like); vehicle or aeronautical control devices systems and components thereof (e.g., navigation devices, safety devices or controllers, security devices, and the like); corporate or business infrastructure devices or appliances (e.g., private branch exchange devices, voice-over internet protocol hosts and controllers, end-user terminals, and the like); personal electronic devices and systems and components thereof (e.g., cellular phones, tablet computers, desktop computers, laptop computers, wearable devices); personal electronic devices and accessories thereof (e.g., peripheral input devices, wearable devices, implantable devices, medical devices and so on); and so on. It may be appreciated that the foregoing examples are not exhaustive.

As described herein, the term "processor" refers to any software and/or hardware-implemented data processing device or circuit physically and/or structurally configured to instantiate one or more classes or objects that are purpose-configured to perform specific transformations of data including operations represented as code and/or instructions included in a program that can be stored within, and accessed from, a memory. This term is meant to encompass a single processor or processing unit, multiple processors, multiple processing units, analog or digital circuits, or other suitably configured computing element or combination of elements.

In view of the foregoing, and for simplicity of description and illustration, the electronic device 200 depicts the interface pressure sensor system 204 communicably coupled to a processing resource 206.

The electronic device 200 can further or optionally include one or more memory resources 208, a display 210, and one or more input/output systems 212. Examples of each of these components are provided above with reference to FIGS. 1A-1F; this description is not repeated.

The interface pressure sensor system 204 can itself include a sensor interface 214 that is configured to communicably couple to the processing resource 206 of the electronic device 200. As noted above, the sensor interface 214 can be configured in any suitable manner. The sensor interface 214 can be configured for parallel or serial output, for current or voltage output, for high frequency or low frequency output and so on. The sensor interface 214 can be configured in any suitable way. For simplicity of description, many embodiments that follow reference and/or contemplate a sensor interface 214 configured to implement a standards-compliant communications protocol, such as I2C or USB.

The sensor interface 214 is communicably coupled to one or more groups 216 of one or more individual pressure sensor modules 218, both of which are described in greater detail blow. In some cases, the sensor interface 214 is directly coupled to each individual pressure sensor module, whereas in other constructions, the sensor interface 214 is coupled to a controller that, in turn, is coupled to each individual pressure sensor module. In some cases, each group of pressure sensor modules can include a dedicated controller that is configured to receive and pre-process one or more outputs of one or more of the sensors of that group. It may be appreciated by a person of skill in the art that many configurations and communications/sensing architectures are possible.

In some embodiments, an interface pressure sensor system (such as the interface pressure sensor systems depicted and referenced in FIGS. 1A-1F) can include one or more self-calibration sensors, routines, or submodules or subsystems. For example, in the illustrated embodiment, the interface pressure sensor system further optionally includes a thermal calibration subsystem 220 that can include one or more absolute or relative temperature sensors, output from which can be used to thermally calibrate an output of one or more of the pressure sensor modules.

More specifically, output from a temperature sensor associated with an interface pressure sensor system as described herein can be used to modify samples of an electrical property (e.g., resistance, capacitance, inductance, resonance frequency, and so on) of the interface pressure sensor system or a module thereof. In other cases, output from the temperature sensor can be used to modify a higher-order value calculated or otherwise obtained once the interface pressure sensor module has been sampled (e.g., by an application specific integrated circuit). In other words, in a more simple phrasing, temperature calibration can be performed against raw output of an interface pressure sensor, whether digital or analog, and/or temperature calibration can be performed against downstream values dependent on raw output of an interface pressure sensor, such as a biometric value or characteristic (e.g., blood pressure, pulse wave velocity, pulse transit time, and so on).

A temperature sensor can be formed with and/or otherwise integrated with sensing electronics of an interface pressure sensor system (or any module thereof), or in other constructions may be a separate component conductively and thermally coupled to one or more portions of the interface pressure sensor system. This is merely one example of a calibration subsystem; other implementations can include other types of calibration systems including, but not limited to: factory calibration lookup tables; field calibrations by software; humidity calibrations; user-specific calibrations; and so on.

In yet further examples, one or more calibration sensors or systems can be leveraged for a different or additional purpose; for example, a thermal calibration temperature sensor may be used to determine an ambient temperature. In some cases, the ambient temperature reading can be correlated to and/or may be leveraged as a body temperature reading of a user/wearer of a wearable electronic device incorporating the interface pressure sensor system. For example, FIG. 1D can incorporate an interface pressure sensor system as described herein in which a first pressure sensing signal is leveraged to receive user input, a second pressure sensing signal is leveraged to determine a blood pressure, a pulse transit time, and/or a pulse wave velocity of a user/wearer of the electronic device, and a temperature sensor signal can be used to determine (or estimate) the user/wearer's core body temperature, radial artery temperature, basal body temperature, skin temperature, or any other suitable body temperature.

In this manner, and in these constructions, a wearable electronic device incorporating an interface pressure sensor system as described herein can be used to obtain user input, one or more biometric and/or health parameters, or a combination thereof. In still further examples, a temperature sensor can be used to determine a user input (e.g., a user resting a finger on a headphone device may temporarily locally increase temperature), an operational mode of the wearable electronic device (e.g., whether the device is being worn or not), or for any other suitable calibration or sensing purpose.

For example, as noted above, an interface pressure sensor system can be integrated into a wrist-worn wearable electronic device (see, e.g., FIG. 1E). In this implementation, the interface pressure sensor system can define a sensing surface configured to interface with a radial skin surface of a wearer of that device. As a result of this construction and placement, the interface pressure sensor system defines a pressure sensing surface that interfaces with, and/or partially aligns with (and/or extends perpendicular to, in order to increase alignment tolerance) the wearer's radial artery. In this manner, the interface pressure sensor system can be used to detect pressure waves resulting from the wearer's pulse and, based on sampling the pressure wave, can determine, estimate, or otherwise calculate the wearer's blood pressure, pulse transit time, pulse wave velocity, and so on. In addition, the interface pressure sensor system can include one or more temperature sensors, such as noted above. The temperature sensor(s) can be used to calibrate output from the interface pressure sensor to improve the accuracy, precision, and temperature-independence of measurements and biometric statistics determined therefrom. In addition or in the alternative, the temperature sensor(s) can be used to determine a skin temperature of the wearer's wrist. The skin temperature of the wearer's wrist can thereafter be correlated to core body temperature, radial artery temperature, basal body temperature, or any other temperature-based or temperature-informed biometric characteristic of the wearer. In addition, the temperature sensor can be used as a low-power sensor to determine if and when the wearer begins wearing the wearable electronic device; temperature can serve as a proxy for other means of determining that a user is actually wearing the wearable electronic device. In other examples, temperature samples and/or data can serve as a proxy for determining a quality of contact between the interface pressure sensor and a user's skin surface.

In yet other examples, a temperature sensor may be used as user input device. For example, as noted above, the user may place a hand or finger over a portion of the wearable electronic device, thereby causing a local rise in temperature that can be detected by the temperature sensor(s). This rise in temperature (whether absolute or as a rate of change over time) can be compared against one or more thresholds to determine whether a user input is intended. In this manner, a wrist-worn wearable electronic device can be configured to accurately determine blood pressure, core body temperature, radial artery temperature, skin temperature, pulse transit time, pulse wave velocity, and so on, with a single temperature-calibrated interface pressure sensor system, such as described herein and shown in FIGS. 1A-2. More generally, an interface pressure sensor system as described herein can, when incorporated into a wrist-worn electronic device, can be used as a biometric sensor, a user input sensor, a use/wearing sensor, and/or an ambient temperature sensor.

In other example constructions, such as shown in FIG. 1F, an interface pressure sensor system as described herein can be placed in an in-bed sleep sensor. In such cases, as with the wearable electronic device examples described above, the in-bed sensor can be configured to obtain, without limitation: respiration rate; bed movement; sleep state; pulse; temperature; bed occupancy; and so on. In these examples, as with the wearable electronic device examples presented above, pressure information and temperature information can be leveraged collectively and/or separately for input sensing purposes, for biometric sensing purposes, for calibration purposes, for ambient environment sensing (e.g., motion, temperature, and so on).

In yet other examples, an interface pressure sensor system including one or more temperature sensors, such as described above and elsewhere herein, can be incorporated into other wearable devices, clothing, personal accessories, furniture, vehicle seats, and so on to provide occupancy sensing, biometric sensing, pressure sensing, pressure/force-based user input sensing, ambient temperature sensing, body temperature sensing, skin temperature sensing, core body temperature sensing, radial artery temperature sensing, thermal input sensing, skin contact and/or skin contact quality sensing, and so on.

These foregoing embodiments depicted in FIGS. 1A-2 and the various alternatives thereof and variations thereto are presented, generally, for purposes of explanation, and to facilitate an understanding of various configurations and constructions of a system, such as described herein. However, it will be apparent to one skilled in the art that some of the specific details presented herein may not be required in order to practice a particular described embodiment, or an equivalent thereof.

Thus, it is understood that the foregoing and following descriptions of specific embodiments are presented for the limited purposes of illustration and description. These descriptions are not targeted to be exhaustive or to limit the disclosure to the precise forms recited herein. To the contrary, it will be apparent to one of ordinary skill in the art that many modifications and variations are possible in view of the above teachings.

Figure 3A:
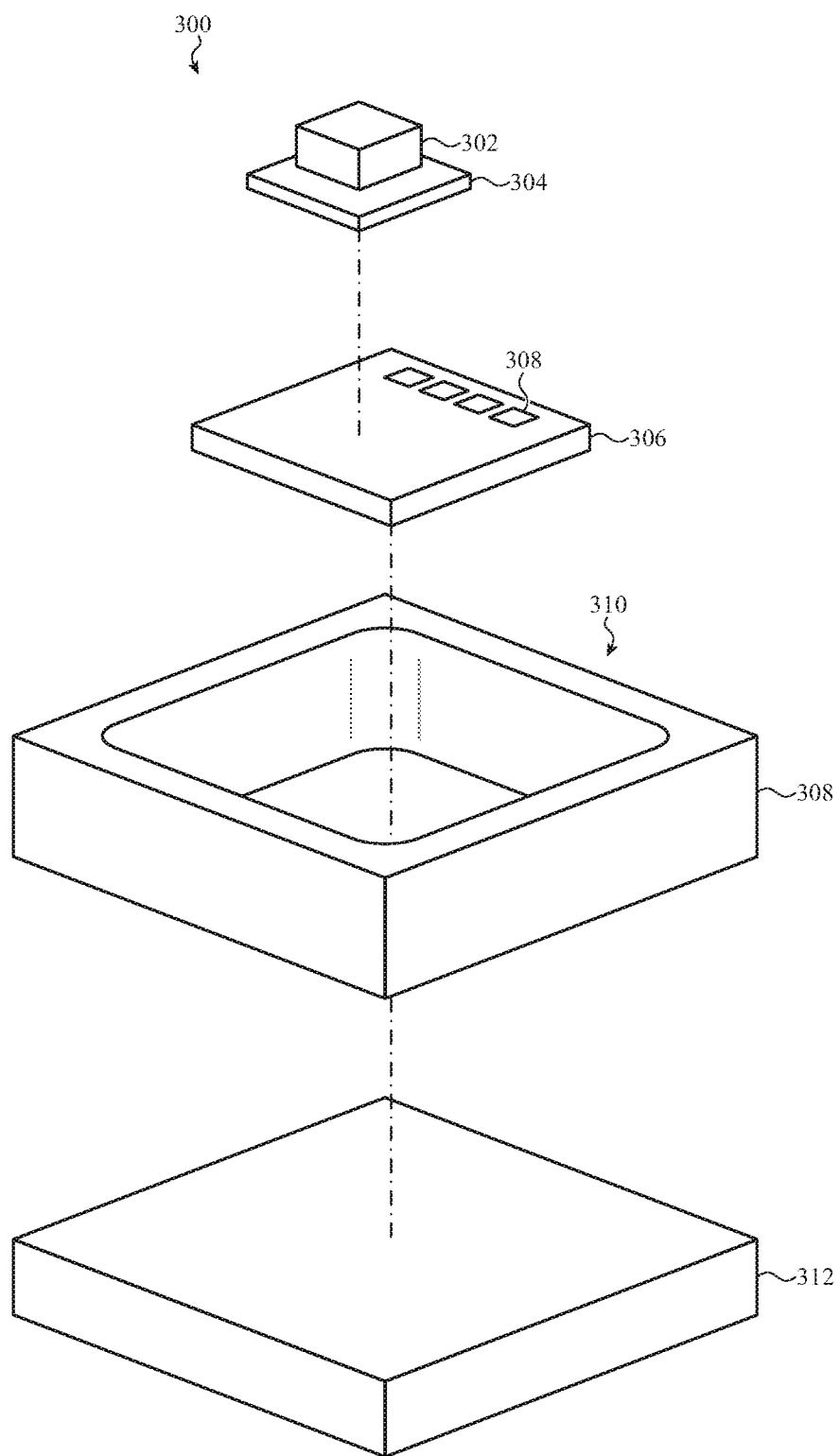
FIG. 3A depicts an assembly diagram of an example pressure sensor module that can form a portion of an interface pressure sensor system, such as described herein.
Figure 3B:
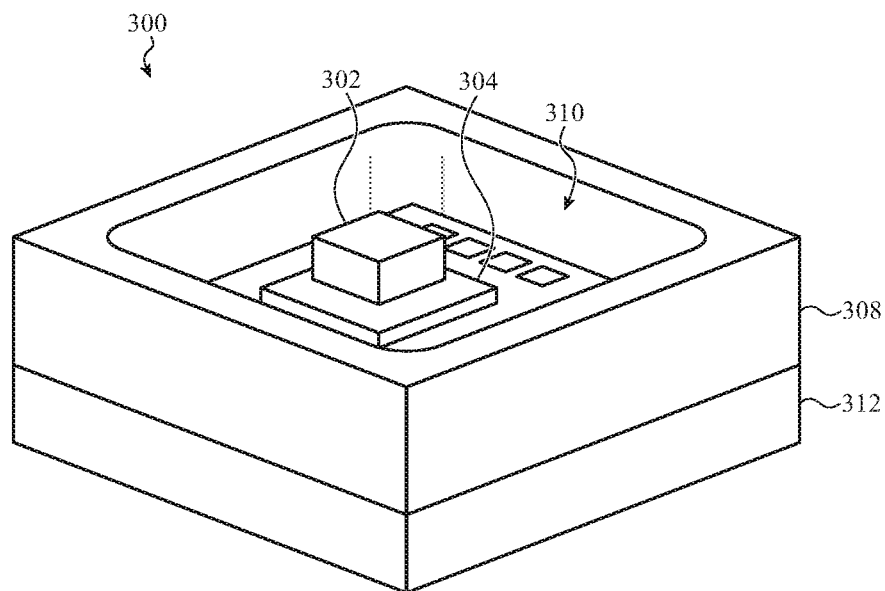
FIG. 3B depicts the pressure sensor module of FIG. 3A, assembled.
Figure 3C:
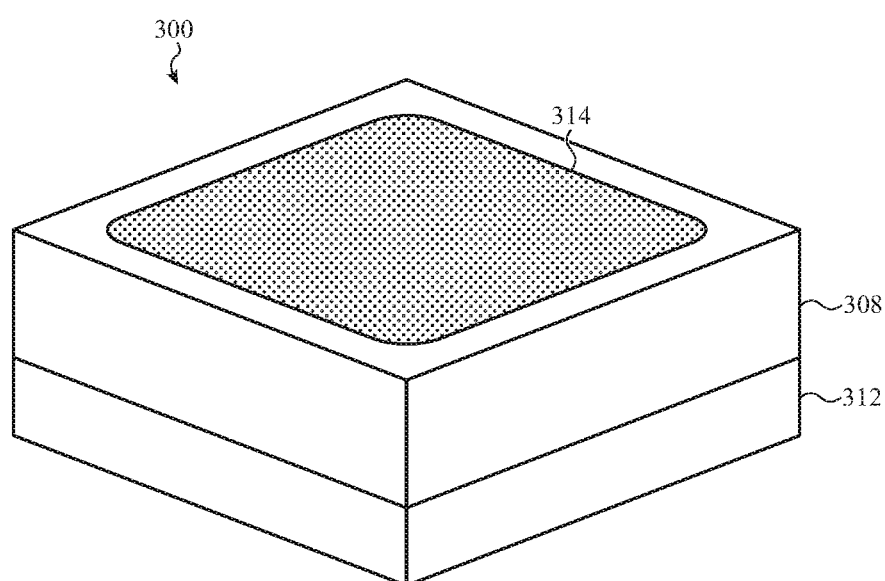
FIG. 3C depicts the pressure sensor module of FIG. 3B, encapsulated with an encapsulation material, potting, or infill material.

Generally and broadly, FIGS. 3A-3C depict a pressure sensor module as described herein. As noted above, a pressure sensor module as described herein generally includes at least three components: a shear wall defining an interior volume; a high-sensitivity pressure sensor, such as a microelectromechanical fluid pressure sensor (e.g., barometer) disposed within the interior volume defined by the shear well; and an encapsulation material filling the interior volume and protecting the fluid pressure sensor.

Although the example constructions depicted in FIGS. 3A-3C reference rectilinear-shaped shear walls and pressure sensor modules, it may be appreciated that this is merely one construction. In other implementations, triangular shear walls may be chosen. In other cases, arbitrary polygonal shapes can be chosen. In still further examples, curved shapes can be chosen including circles, ovals, and the like.

Similarly, the embodiments that follow all reference an encapsulation material cured to exhibit a substantially planar sensing surface. This is also not a requirement of all embodiments. For example in some cases, the encapsulation/infill material can be disposed to exhibit a concave or convex shape. In yet other examples, the sensing surface defined by the encapsulation material can be patterned, textured, or otherwise specially shaped. In some cases, the encapsulation material may a portion of material into which the pressure sensor module is insert molded. For example, with reference to the example embodiment of FIG. 1E, a pressure sensor module as described herein may be insert molded into an elastomeric band configured to couple a wearable electronic device to a user/wearer of that wearable device. In this example, a material selected for the band (e.g., rubber, polymer, fluoroelastomer, and so on) may at least partially fill the interior volume defined by the shear wall, thereby encapsulating the fluid pressure sensor within the interior volume.

These foregoing example embodiments and configurations are not exhaustive of the various configurations of a pressure sensor module, as described herein. To the contrary it may be readily appreciated by a person of skill in the art that a pressure sensor module can be implemented in many ways. Accordingly for simplicity of description and illustration, FIGS. 3A-3C reference an embodiment of a pressure sensor module, as described herein, in which the shear wall takes a substantially rectangular shape.

In particular, FIG. 3A depicts an assembly diagram of an example pressure sensor module that can form a portion of an interface pressure sensor system, such as described herein. The pressure sensor module 300 includes a fluid pressure sensor 302. As noted with respect to other embodiments described herein, the fluid pressure sensor 302 may be a microelectromechanical fluid pressure sensor, such as a high-precision barometric sensor.

In some embodiments, the fluid pressure sensor 302 is implemented as a differential resistance sensor. More specifically, a microelectromechanical structure can define a sealed diaphragm supported by three or more bridges onto which can be disposed resistive sensors. As a result of this construction, when ambient air pressure changes, pressure within the cavity deforms the diaphragm and imparts a strain to the resistive sensors, in turn changing the electrical resistance thereof. By measuring these resistors in a Wheatstone bridge configuration (or a more simple voltage divider configuration), an amount of ambient pressure can be accurately determined.

The fluid pressure sensor 302 is typically formed or coupled onto a breakout board or other intermediate substrate 304 that includes one or more electrical contacts configured to conductively couple the fluid pressure sensor 302 to an electrical circuit.

In some cases, the fluid pressure sensor 302 and the intermediate substrate 304 can be coupled to an application-specific integrated circuit 306. The application-specific integrated circuit 306 can include any suitable digital or analog circuitry configured obtain one or more samples or measurements from the fluid pressure sensor 302. In some cases, the application-specific integrated circuit 306 can be further configured to calibrate and/or unit convert an output of the fluid pressure sensor 302. For example, in some cases, the fluid pressure sensor 302 may be a resistive sensor. As a result, a measurement of the fluid pressure sensor 302 by the application-specific integrated circuit 306 may be in the form of a voltage within a range (e.g., a range from circuit ground to supply voltage, such as 3.3V or 5.0V), a current within a range, or may be in the form of a resistance having units in Ohms. In such examples, the application-specific integrated circuit 306 may be configured to convert these electrical quantity values into a digital or analog value corresponding to a pressure measurement obtained from the fluid pressure sensor 302. In a more simple phrase, the application-specific integrated circuit 306 may be configured to unit convert an electrical quantity into a quantity convertible into Newtons or Pascals.

The application-specific integrated circuit 306 may also implement one or more communications protocols, such as I2C or USB. This standardization of communication can facilitate coupling the application-specific integrated circuit 306 to additional circuitry or computational resources more easily. In particular, to communicably and conductively couple the application-specific integrated circuit 306 to other circuitry, the application-specific integrated circuit 306 can include, and/or may be associated with, one or more electrodes 306a, which may be hot bar pads in certain constructions.

The pressure sensor module 300 further includes a module enclosure 308. The module enclosure 308 in this illustrated example is formed from a rigid material such as glass, fiberglass, metal, plastic, and the like.

The module enclosure 308, as with other embodiments described herein, is configured to protect the fluid pressure sensor 302 from shear forces. In other words, the module enclosure 308 is configured to leverage its rigidity to redirect any shear force applied to the pressure sensor module 300 away from the normal axis of the fluid pressure sensor 302.

In the illustrated embodiment, the module enclosure 308 defines an enclosed polygonal shape, with four sides. An interior sidewall of the module enclosure 308 is depicted as rounded, but this may not be a requirement of all embodiments.

More generally, the module enclosure 308 has a ring or annular shape that encloses an interior volume 310. The interior volume 310 is defined, at least in part, by the interior sidewall of the module enclosure 308. This configuration is not required of all embodiments; in some cases, the module enclosure 308 can define a bucket shape that includes both a sidewall and a lower support surface that may be configured to receive the fluid pressure sensor 302 and/or the application-specific integrated circuit 306.

The module enclosure 308 can be monolithic, or may be made from multiple materials or multiple layers of materials. In some cases, the module enclosure 308 can be textured along the interior sidewall surface to facilitate bonding with an encapsulation material (not shown in FIG. 3A).

The module enclosure 308 is shown with vertical exterior and interior sidewalls, but this is not a requirement of all embodiments. In some examples, a cross-section of the module enclosure 308 may have a trapezoidal shape, being wider at a top edge than at a bottom edge, or vice versa. In other cases, other cross-sections may be appropriate.

In many constructions, although not required, the module enclosure 308 can be disposed over a rigid substrate 312. In this manner, the rigid substrate 312 and the module enclosure 308 cooperate to define a partially closed volume (e.g., the interior volume 310). More specifically, in the illustrated embodiment, the rigid substrate 312 defines a lower surface of the interior volume 310 and the module enclosure 308 defines side surfaces of the internal volume.

In many embodiments, the rigid substrate 312 is formed from a rigid material such as glass, fiberglass, metal, or plastic. This, however may not be required. For example, in some embodiments, the rigid substrate may include a flexible circuit disposed over a rigid member such as a metal frame or stiffener.

The rigid substrate 312 can include one or more conductive traces configured to conductively and communicably couple the various electrical components of the pressure sensor module 300 to other circuits, processing allocations, or computational elements.

FIG. 3B depicts the pressure sensor module of FIG. 3A, assembled. More specifically, the rigid substrate 312 is coupled to the module enclosure 308 to define the interior volume 310 into which the application-specific integrated circuit 306 can be disposed and electrically coupled to the fluid pressure sensor 302 via the intermediate substrate 304. More specifically, the fluid pressure sensor 302 can be conductively and/or mechanically coupled to one or more of: the intermediate substrate 304; the application-specific integrated circuit 306; the electrodes 306a; and/or the rigid substrate 312.

Regardless of the particular coupling techniques used to conductively and mechanically couple the various components of the pressure sensor module 300, it may be appreciated that each of the illustrated components are suitably mechanically and conductively coupled to one another so as to define a single, self-supporting, electromechanical part. Any suitable coupling techniques can be used, including but not limited to: soldering; adhesives; mechanical fastening; and so on. In certain embodiments, each component can be formed together in a single manufacturing process.

Once assembled as shown in FIG. 3B, the interior volume 310 can be filled with an infill material, such as described above. In particular, FIG. 3C depicts the pressure sensor module of FIG. 3B, encapsulated with an encapsulation material, potting, or infill material identified in the figure as the encapsulation 314.

As noted above, the encapsulation 314 can serve multiple purposes. First, the encapsulation 314 can define a sensing surface that can take any suitable shape. In the illustrated embodiment, the sensing surface is defined as an upper surface of the encapsulation 314. The upper surface is illustrated as opposite the rigid substrate 312. The sensing surface defined by the encapsulation 314 is configured to receive pressure/force input primarily along a direction normal to that surface.

The sensing surface defined by the encapsulation 314 is shown with a planar shape, but as noted above, this is not required. In some cases, the sensing surface may be convex, may sit proud of an upper surface of the module enclosure 308, or may be debossed/sunken in relative to the module enclosure 308.

The encapsulation 314 can be made from any number of suitable materials, although in many examples polymers or plastics are selected. Due to the fragile nature of the structure(s) that may define the fluid pressure sensor 302, the encapsulation 314 may be formed from a low-set thermoplastic. Similarly the encapsulation 314 may be formed from a low-compression set material.

The encapsulation 314 may be selected at least in part based on a coupling coefficient with the fluid pressure sensor 302. In other words, a durometer measurement or other property of the cured material forming the encapsulation 314 may be selected so as to mechanically couple to the fluid pressure sensor 302 most efficiently.

In some cases, the encapsulation 314 can be disposed into the interior volume 310 as a liquid which is thereafter cured. In some cases, prior to curing, the pressure sensor module 300 with uncured encapsulant may be placed in an autoclave or vacuum chamber to remove latent air pockets.

In some cases, at least a portion of cured encapsulant/infill may be machined away or otherwise removed after curing.

In some cases, the encapsulation 314 may be only partially cured in a first operation so that the pressure sensor module 300 can be handled. Thereafter, once the pressure sensor module 300 is positioned in a final assembled location, the encapsulation 314 may be fully cured.

These foregoing examples and descriptions of example manufacturing techniques are not exhaustive of the ways in which a pressure sensor module, such as described herein, can be formed. Accordingly, it may be appreciated that many variations of and additions to the foregoing described example are within the scope of the disclosure provided herein. More broadly it may be appreciated that these foregoing embodiments depicted in FIGS. 3A-3C and the various alternatives thereof and variations thereto are presented, generally, for purposes of explanation, and to facilitate an understanding of various configurations and constructions of a system, such as described herein. However, it will be apparent to one skilled in the art that some of the specific details presented herein may not be required in order to practice a particular described embodiment, or an equivalent thereof.

Thus, it is understood that the foregoing and following descriptions of specific embodiments are presented for the limited purposes of illustration and description. These descriptions are not targeted to be exhaustive or to limit the disclosure to the precise forms recited herein. To the contrary, it will be apparent to one of ordinary skill in the art that many modifications and variations are possible in view of the above teachings.

For example, although a stacked die architecture is depicted in the foregoing figures, such a configuration is not required; in some cases, a sensor module may be positioned adjacent to, below, alongside, or otherwise relative to an application specific integrated circuit. In other cases, a portion of the an application specific integrated circuit can form a portion of a shear wall, as described herein. In yet other cases, an application specific integrated circuit can be attached to or otherwise adhered to a shear wall as described herein. Many configurations are possible.

Generally and broadly, FIGS. 4A-4F illustrate example embodiments in which multiple discrete, individual pressure sensor modules are grouped together to increase an overall area over which pressure or force sensing can be achieved.

In particular, as noted above, a pressure sensor module (such as shown in FIG. 3A-3C) may be implemented in many examples as a small surface mount component. In some examples, a pressure sensor module may be on the order of 2 mm×2 mm, defining a sensing surface area of less than 4 mm². As such, in some embodiments, it may be desirable to increase the sensing surface beyond 4 mm². Although this example dimension is understood as non-limiting (e.g., different implementations can be larger or smaller, or may have a different shape), one such solution to increasing overall sensing area is by grouping, such as described below.

Figure 4A:
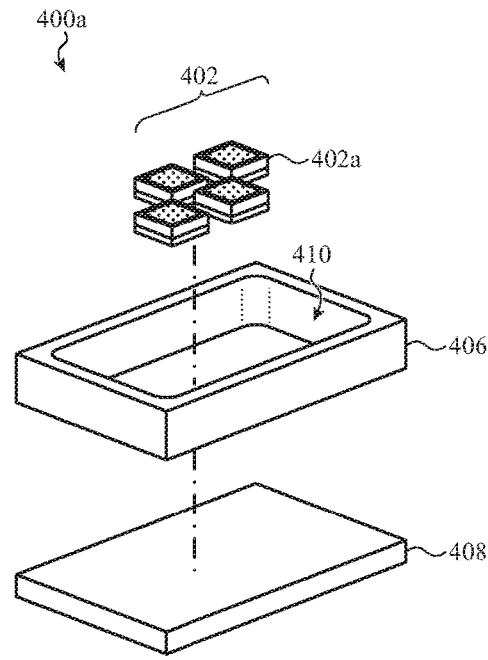
FIG. 4A depicts an assembly diagram of a group of multiple pressure sensor modules such as shown in FIG. 3A, arranged in a pattern.

FIG. 4A depicts an assembly diagram of a group of multiple pressure sensor modules such as shown in FIG. 3A, arranged in a pattern.

In particular, the pressure sensor group 400a includes four independent pressure sensor modules 402, one of which is identified as the pressure sensor module 404. Each of these pressure sensor modules can be configured in the same manner as described above with reference to FIGS. 3A-3C; this description is not repeated.

The four independent pressure sensor modules 402 are arranged in two offsets rows, each with two sensors. As a result of this offset construction, linear position offset sensitivity of the pressure sensor group 400a is decreased. In other words, the pressure sensor group 400a can be positioned relative to a pressure input source—such as a radial artery of a user—with greater ease, because precise alignment is not required as it may be with conventional systems.

The pressure sensor group 400a also includes a module enclosure 406 which may be similar to, but larger than, the individual module enclosures of each individual pressure sensor module.

The module enclosure/shear wall 406 in this illustrated example is formed from a rigid material such as glass, ceramic, fiberglass, metal, plastic, and the like. The module enclosure/shear wall 406, as with other embodiments described herein, is configured to protect the four independent pressure sensor modules 402 from shear forces, providing additional shear force support over the individual module enclosures/shear walls associated with each individual module. In other words, the module enclosure/shear wall 406 is configured to leverage its rigidity to redirect any shear force applied to the pressure sensor module 300 away from the normal axis of each of the four independent pressure sensor modules 402.

As with the individual modules it protects, the module enclosure/shear wall 406 defines an enclosed polygonal shape, with four sides. An interior sidewall of the module enclosure/shear wall 406 is depicted as rounded, but this may not be a requirement of all embodiments. In some cases, the module enclosure/shear wall 406 takes a different shape than the module enclosures of the four independent pressure sensor modules 402, but this is not required.

More generally, the module enclosure/shear wall 406 is coupled to a rigid substrate 408 and has a ring or annular shape that encloses an interior volume 410. The interior volume 410 is defined, at least in part, by the interior sidewall of the module enclosure/shear wall 406. This configuration is not required of all embodiments; in some cases, the module enclosure/shear wall 406 can define a bucket shape that includes both a sidewall and a lower support surface that may be configured to receive the four independent pressure sensor modules 402.

The module enclosure/shear wall 406 can be monolithic, or may be made from multiple materials or multiple layers of materials. In some cases, the module enclosure/shear wall 406 can be textured along the interior sidewall surface to facilitate bonding with an encapsulation material (not shown in FIG. 4A, see, e.g., FIGS. 4D-4F).

The module enclosure/shear wall 406 is shown with vertical exterior and interior sidewalls, but this is not a requirement of all embodiments. In some examples, a cross-section of the module enclosure/shear wall 406 may have a trapezoidal shape, being wider at a top edge than at a bottom edge, or vice versa. In other cases, other cross-sections may be appropriate.

In many constructions, although not required, the module enclosure/shear wall 406 can be disposed over the rigid substrate 408. In this manner, the rigid substrate 408 and the module enclosure/shear wall 406 cooperate to define a partially closed volume (e.g., the interior volume 410). More specifically, in the illustrated embodiment, the rigid substrate 408 defines a lower surface of the internal volume 410 and the module enclosure/shear wall 406 defines side surfaces of the internal volume.

In many embodiments, the rigid substrate 408 is formed from a rigid material such as glass, fiberglass, metal, or plastic. This, however may not be required. For example, in some embodiments, the rigid substrate may include a flexible circuit disposed over a rigid member such as a metal frame or stiffener.

The rigid substrate 408 can include one or more conductive traces configured to conductively and communicably couple the various electrical components of the four independent pressure sensor modules 402 to other circuits, processing allocations, or computational elements.

Figure 4B:
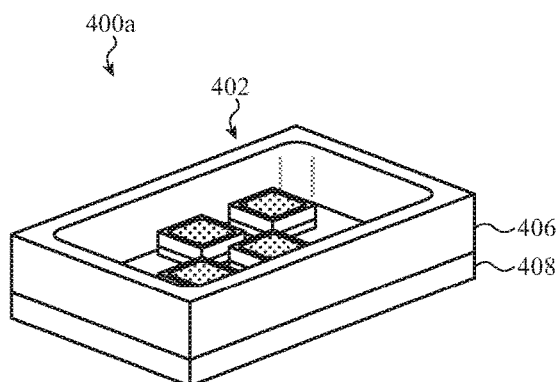
FIG. 4B depicts the group of FIG. 4A, assembled.

FIG. 4B depicts the pressure sensor module of FIG. 4A, assembled. More specifically, the rigid substrate 408 is coupled to the module enclosure 406 (e.g., via mechanical fasteners, adhesives, and so on) to define the interior volume 410 into which the four independent pressure sensor modules 402 can be disposed.

More specifically, the four independent pressure sensor modules 402 can be conductively and/or mechanically coupled to the rigid substrate 408. In some embodiments, the rigid substrate 408 can further include one or more circuits or circuit components, such as an application-specific integrated circuit. For simplicity of description, these circuit elements can be collectively referred to as a "controller" or group controller disposed on the rigid substrate 408. The controller can be coupled onto the rigid substrate 408 within the interior volume 410 or outside of the rigid substrate 408, such as on a lower surface of the rigid substrate 408. In some cases, one or more circuit components of the controller can be disposed within the rigid substrate 408 itself (e.g., vias, multi-layered circuit board components, and so on). The controller can be configured to communicably and/or conductively couple to one or more of the four independent pressure sensor modules 402.

In some examples, the controller can be configured to regularly sample each of the four independent pressure sensor modules 402 in order to determine which of the four independent pressure sensor modules 402 is presently receiving the strongest pressure wave signal. In such a configuration, the controller may be configured to select only a single pressure sensor module's output to provide to other processing circuitry coupled to the group.

In other cases, the controller can be configured to average two or more outputs of the four independent pressure sensor modules 402. In other cases, the controller can be configured to select a module outputting a signal with noise below a threshold. Many suitable configurations and operational modes are possible.

These foregoing example embodiments are not exhaustive; any suitable processing, signal processing, or sampling technique can be implemented by a controller such as described above and herein, elsewhere.

As with previously-described embodiments, regardless of the particular coupling techniques used to conductively and mechanically couple the various components of the pressure sensor group 400a, it may be appreciated that each of the illustrated components are suitably mechanically and conductively coupled to one another so as to define a single, self-supporting, electromechanical part. Any suitable coupling techniques can be used, including but not limited to: soldering; adhesives; mechanical fastening; and so on. In certain embodiments, each component can be formed together in a single manufacturing process.

In many examples, a height of the module enclosure 406 may be greater than a height of the four independent pressure sensor modules 402, such as shown in FIG. 4B. This, however is not a required. In other cases, such as shown in FIG. 4B, a pressure sensor group 400b can be disposed within a module enclosure 406 having the same height as the four independent pressure sensor modules 402.

Figure 4C:
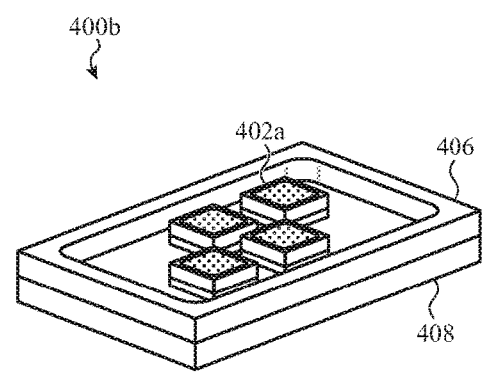
FIG. 4C depicts an alternative configuration of the group of FIG. 4A, assembled.
Figure 4D:
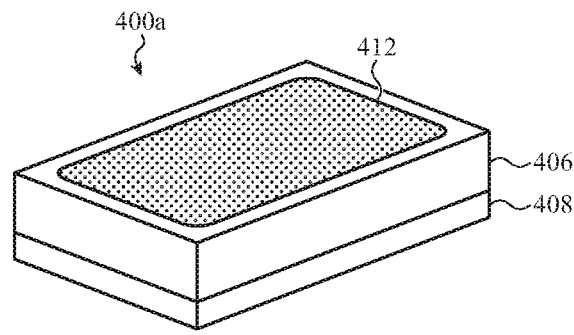
FIG. 4D depicts the group of FIG. 4B, encapsulated with an encapsulation material, potting, or infill material.
Figure 4E:
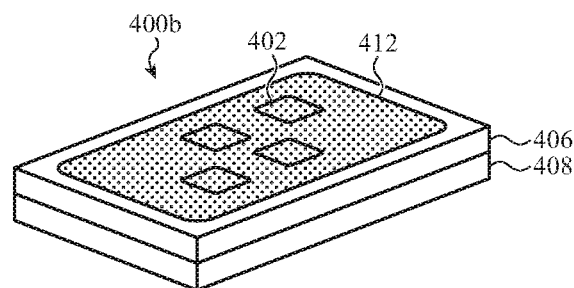
FIG. 4E depicts the group of FIG. 4C, encapsulated with an encapsulation material, potting, or infill material.
Figure 4F:
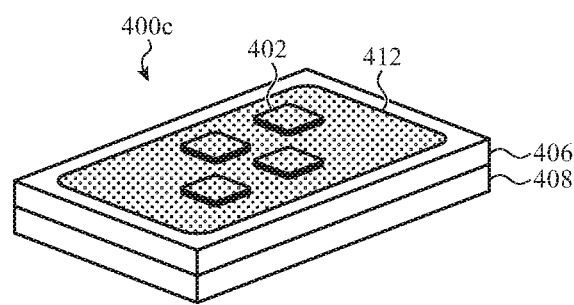
FIG. 4F depicts an alternative configuration of the group of FIG. 4C, encapsulated with an encapsulation material, potting, or infill material.

Once assembled as shown in FIG. 4B or 4C, the interior volume 410 can be filled with an infill material, such as described above. In particular, FIGS. 4D-4F depict the pressure sensor groups of FIGS. 4B-4C (the pressure sensor group 400a and pressure sensor group 400b, respectively), encapsulated with an encapsulation material, potting, or infill material identified in the figure as the encapsulation 412.

As noted above, the encapsulation 412 can serve multiple purposes. First, as with other embodiments described herein, the encapsulation 412 can define a sensing surface that can take any suitable shape. In the illustrated embodiments, the sensing surface is defined by an upper surface of the encapsulation 412. The upper surface is illustrated as opposite the rigid substrate 408. The sensing surface defined by the encapsulation 412 is configured to receive pressure/force input primarily along a direction normal to that surface.

The sensing surface defined by the encapsulation 412 is shown with a planar shape, but as noted above, this is not required. In some cases, the sensing surface may be convex, may sit proud of an upper surface of the module enclosure 406, or may be debossed/sunken in relative to the module enclosure 406.

As described above with reference to FIGS. 3A-3C, the encapsulation 412 can be made from any number of suitable materials, although in many examples polymers or plastics are selected. Due to the fragile nature of the structure(s) that may define the four independent pressure sensor modules 402, the encapsulation 412 may be formed from a low-set thermoplastic. Similarly the encapsulation 412 may be formed from a low-compression set material.

The encapsulation 412 may be selected at least in part based on a coupling coefficient with the encapsulation materials of the four independent pressure sensor modules 402. In other words, a durometer measurement or other property of the cured material forming the encapsulation 412 may be selected so as to mechanically couple to the four independent pressure sensor modules 402 most efficiently. In some cases, the encapsulation 412 may be the same material as the encapsulation materials of the four independent pressure sensor modules 402, but this is not required. In some cases, the encapsulation 412 may be a higher durometer polymer, in other cases, it may be a lower durometer polymer. In stull other embodiments, the encapsulation may be an acrylic material.

In still further examples, the encapsulation 412 can be replaced with a rigid housing defining one or more apertures through which at least a portion of the individual sensing surfaces of the four independent pressure sensor modules 402 can extend. The rigid housing can be made from any suitable material, including plastics, metals, and so on.

In some cases, the encapsulation 412 can be disposed into the interior volume 410 as a liquid which is thereafter cured. In some cases, prior to curing, the pressure sensor module 400 with uncured encapsulant may be placed in an autoclave or vacuum chamber to remove latent air pockets. In some cases, at least a portion of cured encapsulant/infill may be machined away or otherwise removed after curing.

In some cases, the encapsulation 412 may be only partially cured in a first operation so that the pressure sensor module 400 can be handled. Thereafter, once the pressure sensor module 400 is positioned in a final assembled location, the encapsulation 412 may be fully cured.

The encapsulation 412 may be disposed to cover at least a portion of the four independent pressure sensor modules 402, such as shown in FIG. 4D. In other cases, it may be disposed to meet an upper surface (the sensing surface) of the four independent pressure sensor modules 402, such as shown in FIG. 4E. In yet other cases, the encapsulation 412 may be disposed below the four independent pressure sensor modules 402, such that the four independent pressure sensor modules 402 sit proud of the encapsulation 412.

These foregoing embodiments depicted in FIGS. 4A-4F and the various alternatives thereof and variations thereto are presented, generally, for purposes of explanation, and to facilitate an understanding of various configurations and constructions of a system, such as described herein. However, it will be apparent to one skilled in the art that some of the specific details presented herein may not be required in order to practice a particular described embodiment, or an equivalent thereof.

Thus, it is understood that the foregoing and following descriptions of specific embodiments are presented for the limited purposes of illustration and description. These descriptions are not targeted to be exhaustive or to limit the disclosure to the precise forms recited herein. To the contrary, it will be apparent to one of ordinary skill in the art that many modifications and variations are possible in view of the above teachings.

For example, in some cases, groups of pressure sensor modules can be arranged in arrays to further increase sensing area. Generally and broadly, FIGS. 5A-6C depict various arrangements of groups of pressure sensor modules, as described herein. Each of these arrays of groups of pressure sensor modules can define a different and implementation-specific sensing area.

Figure 5A:
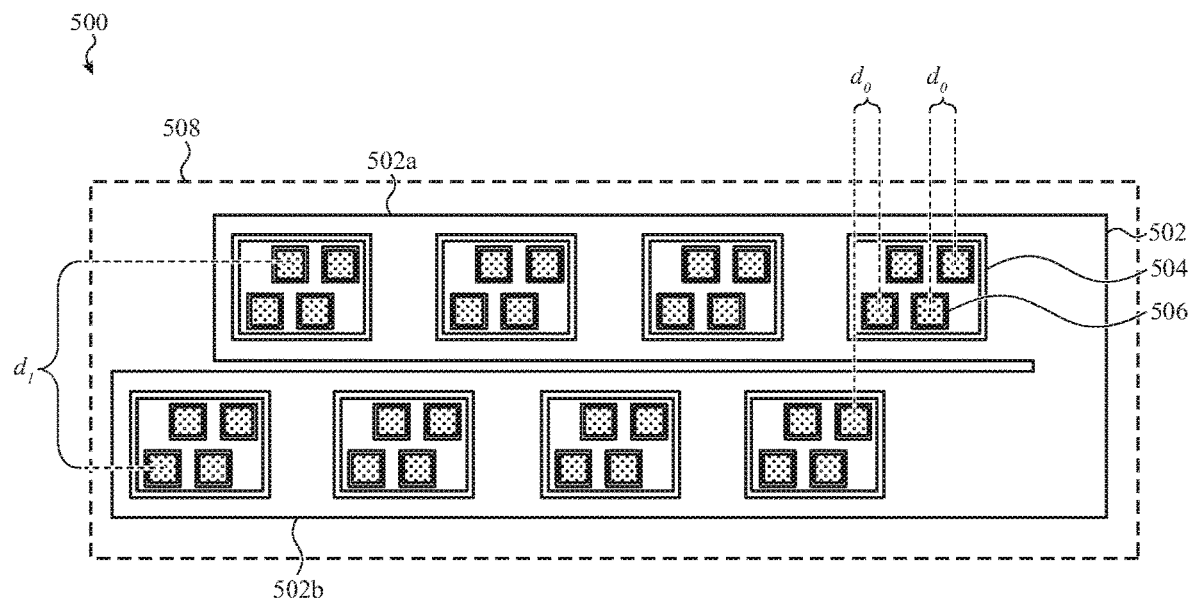
FIG. 5A depicts a plan view of an interface pressure sensor system including an array of groups of pressure sensor modules, such as shown in FIG. 4F.

In particular, FIG. 5A depicts a plan view of an interface pressure sensor system including an array of groups of pressure sensor modules, such as shown in FIG. 4F.

The interface pressure sensor system 500 includes an array of groups of pressure sensor modules. The array is arranged in two linear rows, offset from one another. In particular, each group of pressure sensor modules of a first row of the array is disposed onto a first linear portion 502a of a flexible circuit 502. A second row the array is disposed onto a second linear portion 502b of the flexible circuit 502.

As a result of this offset configuration, the interface pressure sensor system 500 can be leveraged to sense pressure input across a wide area. More specifically, the flexible circuit 502 can be defined by a length and a width. Each of the first row of the array of groups of pressure sensor modules and the second row of the array of groups of pressure sensor modules extend across the length of the flexible circuit 502 and are arranged in a distributed manner such that a constant pitch $d_0$ separates individual pressure sensor modules along the length of the flexible circuit 502.

More specifically, a group of pressure sensor modules is identified as the group 504. The group 504 includes four individual pressure sensor modules, arranged in two offset rows. The right-most pressure sensor module in the top row of the group 504 is separated from the right-most pressure sensor module in the bottom row of the group 504, which is identified as the pressure sensor module 506. More specifically, these two modules are separated from each other, along the length of the flexible substrate 502 by the pitch $d_0$. In another phrasing, each module of each group is arranged in a rhombic pattern, and the array of groups arranges groups themselves into a repeating rhombic pattern.

This pattern can continue beyond the group 504, as each subsequent group (moving from right to left) is positioned so that at least one pressure sensor module is centered at the constant pitch $d_0$. As a result of this construction and arrangement, the interface pressure sensor system 500 can enjoy linearly uninterrupted sensitivity across the entire length of the flexible substrate 502.

As one example, as noted above, an individual pressure sensor module in some embodiments is 2 mm×2 mm. In this example, the pitch separating each pressures module may be slightly smaller than this dimension, so that redundancy can be achieved by partial overlap of nearest-neighbor modules. For example, a pitch of 1.5 mm may be implemented.

With this example dimension, the interface pressure sensor system 500 depicted in FIG. 5A can extend its linear sensitivity from just 2 mm (the linear sensitivity of a single module) to 48 mm (e.g., 32 individual pressure sensor modules are shown, each separated at a pitch of 1.5 mm yields a total length of uninterrupted sensitivity at 48 mm).

It may be appreciated that this example pitch is merely one example. Similarly, the arrangements shown in each individual group of the depicted array may not be required of all embodiments. Similarly, it may be appreciated that a sensing surface or sensing area can be increased by arranging individual pressure sensor modules in any suitable manner. In some cases, more than four pressure sensor modules can be included in a single, encapsulated, group. In other cases, fewer than four can be included in single encapsulated group.

In yet other examples, groups can be encapsulated together in much the same way that individual modules are encapsulated in groups.

In yet other examples, the flexible circuit 502 can have more than two individual portions. In other cases, the flexible circuit 502 can be supported by a stiffener 508.

In some embodiments the first portion 502*a* and the second portion 502*b* of the flexible circuit 502 can be separated by a particular fixed distance $d_1$. In some constructions, this distance can be leveraged to determine a pulse wave velocity of a pulse wave first detected by a pressure sensor module disposed on the first portion 502*a* and, at a later time, detected by a second pressure sensor module disposed on the second portion 502*b*. It may be readily appreciated by a person of skill in the art that by performing a cross-correlation, an autocorrelation, or any other suitable operation, an absolute time difference between a pressure waveform received at the first module and a second pressure waveform received at the second module can be determined. This time is the propagation time between the first portion 502*a* and the second portion 502*b* which, in turn, can be used with the distance $d_0$ to determine pulse wave velocity.

A person of skill in the art may readily appreciate that such a configuration and arrangement can dramatically increase the usefulness of a sensor module, such as described herein. In particular, in one example embodiment shown in FIG. 5B, the interface pressure sensor system 500 is implemented in a wrist-worn device 510 configured to detect blood pressure when worn on a patient's wrist. In this example, having a linear sensitivity of 48 mm dramatically improves the likelihood that at least one pressure sensor module will be aligned over a patient's radial artery. As a result of reliable alignment of at least one pressure sensor module, the wrist-worn device 510 can be configured to reliably obtain one or more health parameters from the user/wearer/patient, such as blood pressure, heart rate, augmentation index, pulse wave velocity, pulse transit time, and so on. In these examples, communications and/or conductive couplings (e.g., flex circuits, traces) can be disposed within a body and/or length of the wrist-worn device 510 (e.g., insert molded into a wristband) such that the sensing/interface surface of the interface sensor system can interface with an interior surface of a user/wearer's wrist.

In other cases, different arrangements of a sensor module can be arranged in any other suitable pattern and/or signaling flex circuits can be disposed in another way. For example, FIG. 5C depicts a portion of a wearable electronic device 512 that includes an interface pressure sensor system 500 that is defined by an arrangement of fifteen individual pressure sensor module groups, each of which may include a number of individual pressure sensor modules. In this example, a flexible circuit conductively coupling the interface pressure sensor system 500 to circuitry can be at least partially external to a body or other section of the wearable electronic device 512.

Figure 5B:
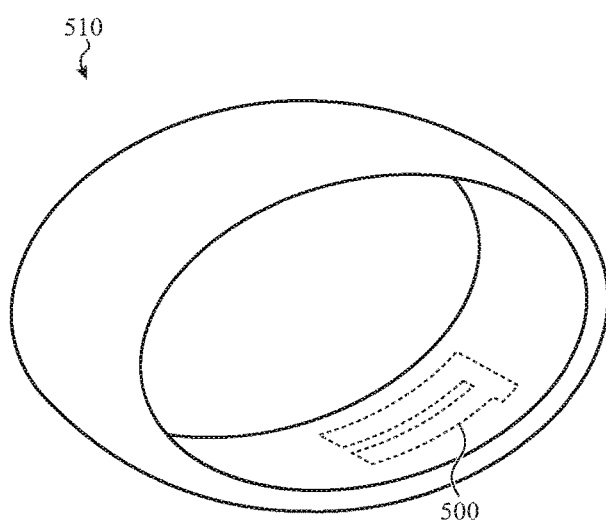
FIG. 5B depicts a wearable electronic device incorporating the interface pressure sensor system of FIG. 5A.
Figure 5C:
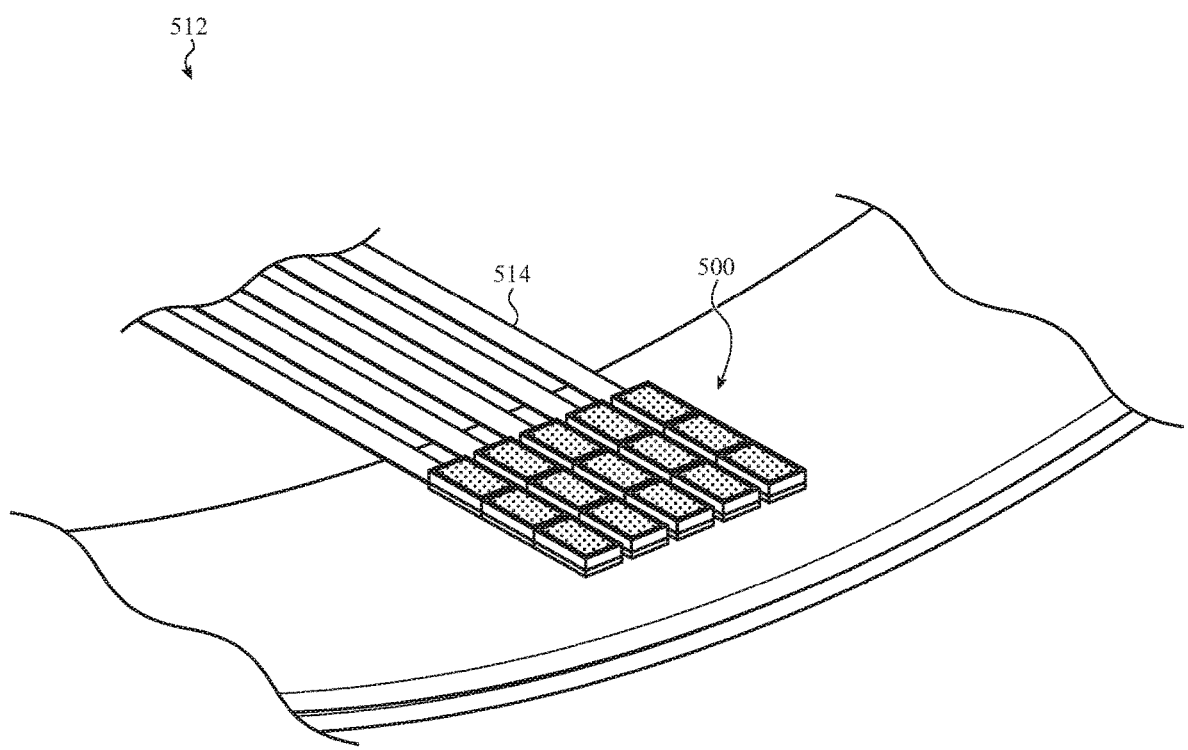
FIG. 5C depicts another wearable electronic device incorporating the interface pressure sensor system of FIG. 5A.

The foregoing embodiment depicted in FIGS. 5A-5C are not exhaustive of the various configurations of arrays of groups of individual pressure sensor modules, as described herein. Similarly, it may be appreciated that the depicted pitch may not be required of all embodiments. In some cases, a larger pitch or a different pattern or arrangement of modules, groups, or arrays may be selected.

Figure 6A:
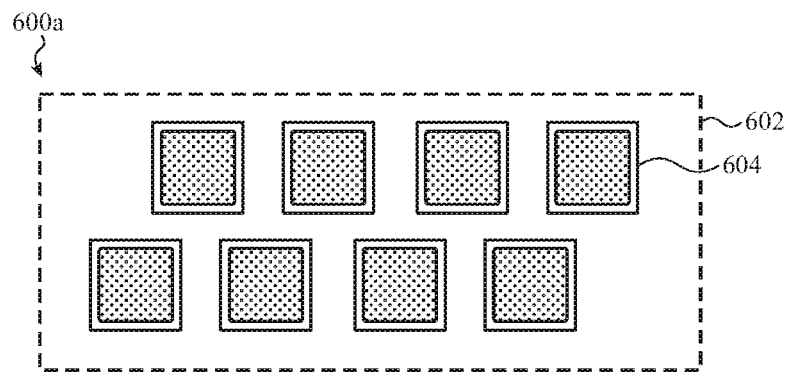
FIGS. 6A-6C each depict an example arrangement of pressure sensor modules.
Figure 6B:
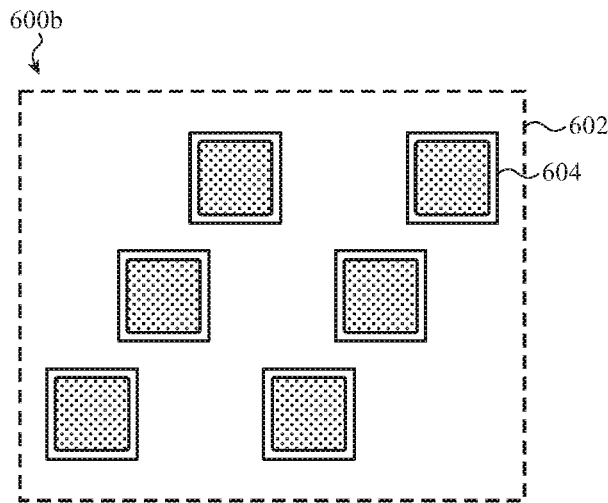
Figure 6C:
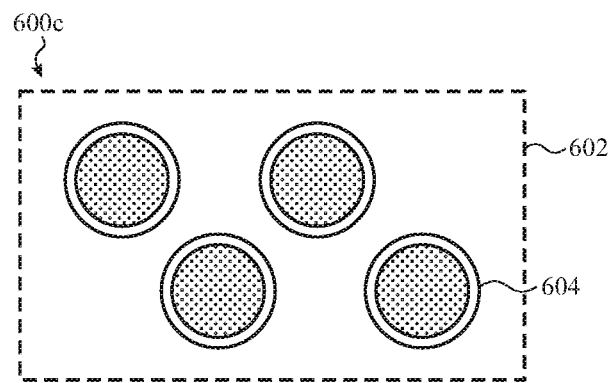

FIGS. 6A-6C each depict an example arrangement of pressure sensor modules and/or pressure sensor module arrays. More specifically, these figures may be understood to depict arrangements of individual pressure sensor modules (e.g. FIGS. 3A-3C) or may likewise be understood to depicted arrangements of encapsulated groups pressure sensor modules (e.g., FIGS. 4A-4F). For simplicity of illustration and description, the term "sensor element" is used to describe either or both a pressure sensor module or a group of pressure sensor modules.

In particular, FIG. 6A depicts an interface pressure sensor system 600*a* defined by an arrangement of sensor elements disposed on a substrate 602, one of which is identified as the sensor element 604. The arrangement depicts two rows of four sensor elements each, offset from one another. The sensor elements can be encapsulated together or not.

FIG. 6B depicts a different interface pressure sensor system 600*b* defined by an arrangement of sensor elements disposed on a substrate 602, one of which is identified as the sensor element 604. In this example, three rows of sensor elements are shown, each offset from another.

FIG. 6C depicts yet a different interface pressure sensor system 600*c* defined by an arrangement of sensor elements disposed on a substrate 602, one of which is identified as the sensor element 604. In this example embodiment, the sensor elements have a circular, instead of square, shape.

In yet other examples, other shapes may be selected. It may be appreciated that any suitable shape is possible, including regular shapes, polygonal shapes, curved shapes, three dimensional shapes (e.g., concave, convex), irregular shapes, These foregoing embodiments depicted in FIGS. 6A-6C and the various alternatives thereof and variations thereto are presented, generally, for purposes of explanation, and to facilitate an understanding of various configurations and constructions of a system, such as described herein. However, it will be apparent to one skilled in the art that some of the specific details presented herein may not be required in order to practice a particular described embodiment, or an equivalent thereof.

Thus, it is understood that the foregoing and following descriptions of specific embodiments are presented for the limited purposes of illustration and description. These descriptions are not targeted to be exhaustive or to limit the disclosure to the precise forms recited herein. To the contrary, it will be apparent to one of ordinary skill in the art that many modifications and variations are possible in view of the above teachings.

Generally and broadly, FIGS. 7-12 are flow charts depicting example operations of methods related to interface pressure sensing systems, as described herein.

Figure 7:
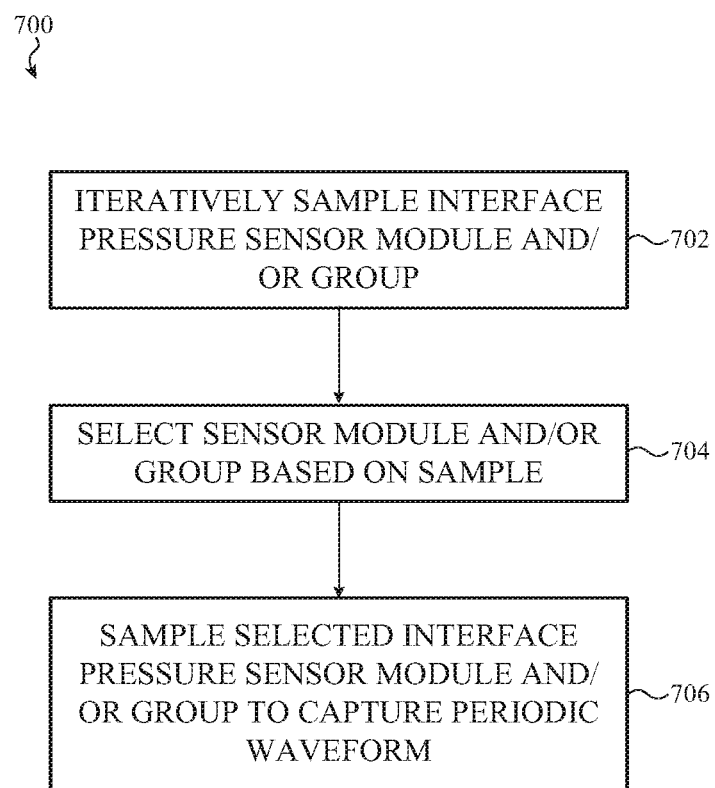
FIG. 7 is a flowchart depicting example operations of a method of sampling an interface pressure sensor system, such as described herein.

FIG. 7 is a flowchart depicting example operations of a method of sampling an interface pressure sensor system, such as described herein.

The method 700 can be performed, whole or in part, by a processor such as described herein. The processor can be ay suitable processor which may be associated with an electronic device, such as described above, or may be an application-specific integrated circuit of an encapsulated pressure sensing module, such as described above. In some cases, at least a portion of the method 700 can be performed by a controller associated with a group of individual pressure sensor modules, such as described above in reference to FIGS. 4A-4F.

The method 700 generally relates to signal selection and filtering. In particular, the method 700 includes operation 702 at which one or more pressure sensor modules or pressure sensor module groups are sampled. In many configurations, the sampled modules are positioned adjacent to one another, but this may not be required of all embodiments.

In some cases, multiple sensors can be sampled simultaneously. In other cases, a multiplexed sensing operation can be performed.

At operation 704, the method 700 can advance to select, among a set of samples obtained from the modules and/or groups at operation 702, which among those provides output of a signal that has a signal-to-noise ratio exceeding a threshold. In other cases, other metrics may be used to determine which among a set of signals, samples, or waveforms may be selected for further processing. In one example, a waveform with a highest peak may be selected. It may be appreciated that any suitable metric, inflection, derived property, or metadata may be used to select a "best" signal from a set of signals received by the processor performing the operation(s) of method 700.

At operation 706, the method 700 advances to obtain samples from only the selected source(s) in order to generate a periodic waveform. In some cases, operation 706 has a different sampling rate than operation 704. In other cases, operation 706 is associated with a different signal processing pipeline than operation 704. For example, operation 706 may include a digital to analog converter, whereas operation 704 processes signals entirely in an analog or frequency domain.

In still further examples, a derived signal can be obtained or created at either of operation 704 or operation 706. An example of a derived signal may be an average of two independent signals. Another derived signal may be a beamformed or phased-array/spatially filtered signal receiving input from multiple signal sources. In yet other examples, a derived signal may be a derivative or integral of any suitable order. In yet other examples, a derived signal may be pre-filtered, such as with a low pass filter, a high pass filter, a band pass filter, or any other suitable infinite impulse response or finite impulse response filter.

Figure 8:
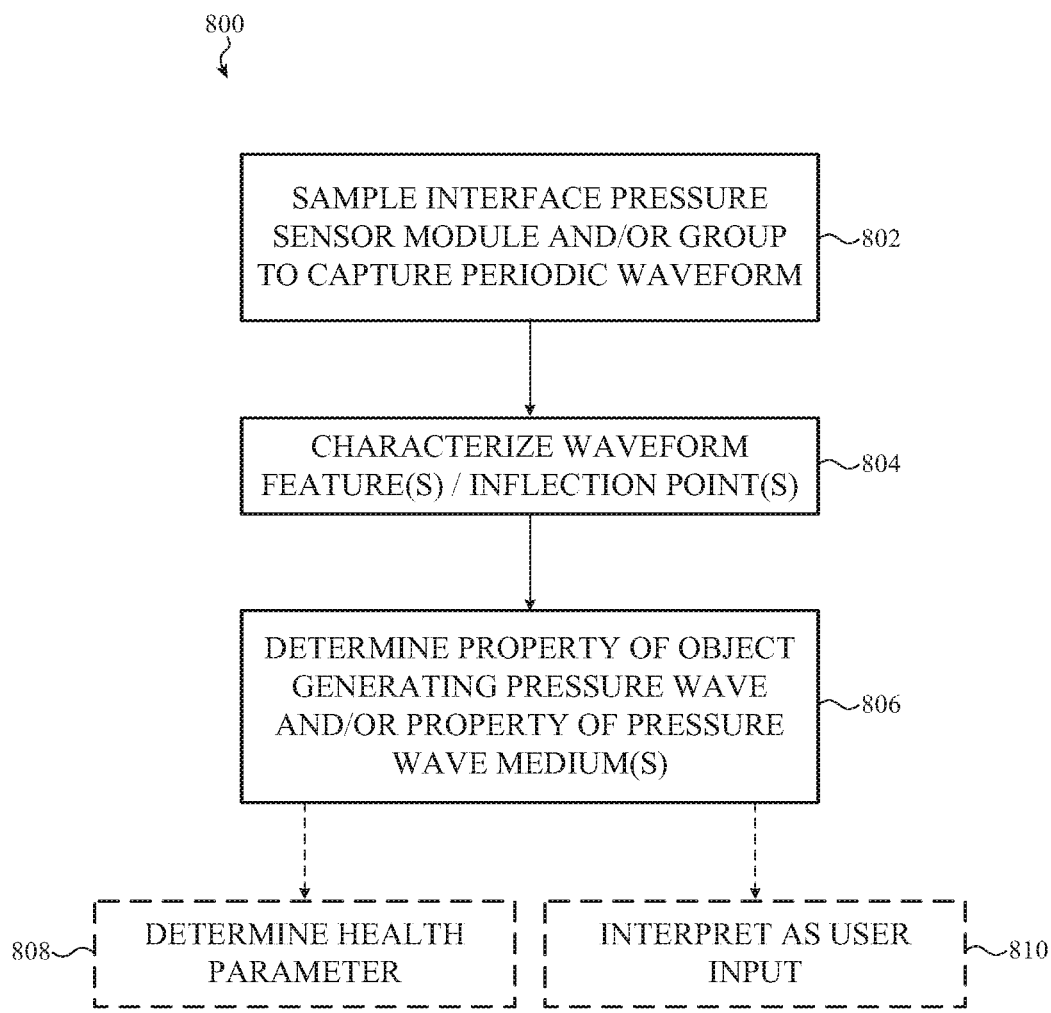
FIG. 8 is a flowchart depicting example operations of a method of leveraging output from an interface pressure sensor system to determine a health parameter or to receive user input, such as described herein.

FIG. 8 is a flowchart depicting example operations of a method of leveraging output from an interface pressure sensor system to determine a health parameter or to receive user input, such as described herein. As with the method of FIG. 7, the method of this figure can be performed by any suitable hardware, software, analog circuitry, or any combination or interoperation thereof. This description is not repeated.

The method 800 includes operation 802 at which a selected module or set of modules is sampled to capture a periodic waveform having a center frequency. The periodic waveform may correspond to a health parameter of a user, such as a pulse or heartrate.

The method 800 includes operation 804 at which the waveform obtained at operation 802 can be analyzed to determine one or more characteristics thereof. For example, statistical analysis may be performed on one or more periods of the periodic waveform to determine one or more inflection points or features of that waveform. As may be appreciated by a person of skill in the art, any number of analyses can be performed against waveform data, and the steps to perform those analyses may vary from embodiment to embodiment and implementation to implementation.

The method 800 further includes operation 806 at which the method 800 advances to determine one or more properties of an object that generated the pressure wave and/or the medium through which that pressure wave propagated. For example, in the case that the method 800 is performed in order to obtain a blood pressure measurement from a user, the pressure wave can be analyzed to determine a blood pressure (either systolic or diastolic or both) value or a median blood pressure that corresponds to the pressure wave sampled at operation 802. In another example, a pulse wave velocity may be determined which in turn can be correlated to an augmentation index of the user/patient. In other cases, the pulse wave velocity can be correlated to a pulse transit time which, in turn, can be correlated proportionately to blood pressure.

In another example, the pressure wave may be associated with a user input. In such examples, the pressure wave can analyzed to determine whether the user applied a single for input or provided a force gesture.

As a result of the operation 806, the method 800 may optionally advance to operation 808 or operation 810. At operation 808, a health parameter of a user may be determined. For example, the blood pressure measurement or pulse measurement obtained at operation 806 can be compared against a health threshold to determine whether that blood pressure measurement is either too high or too low for the particular user. In another example, such as shown/illustrated by operation 810, a user input may be characterized (e.g., single gesture, multi-input gesture, slide gesture, and so on).

Figure 9:
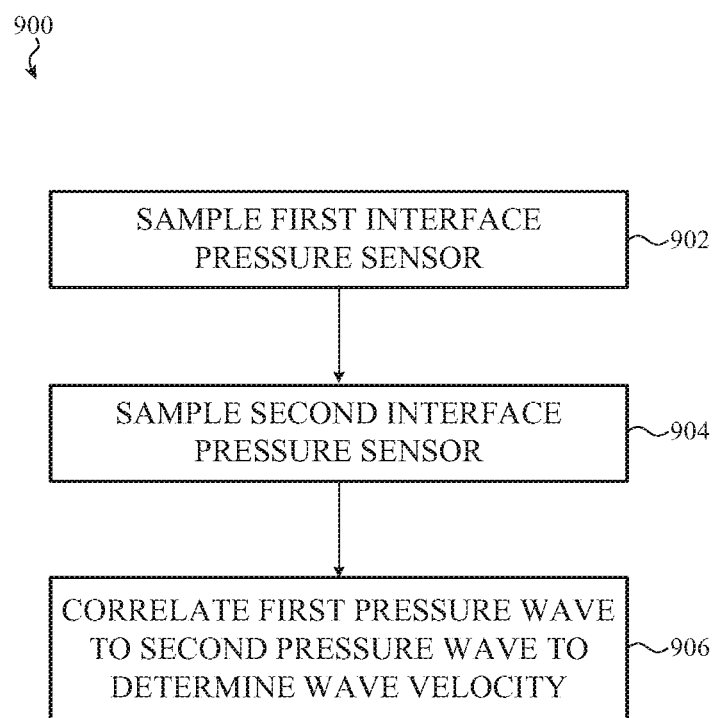
FIG. 9 is a flowchart depicting example operations of a method of determining pressure wave velocity with an interface pressure sensor system, such as described herein.

FIG. 9 is a flowchart depicting example operations of a method of determining pressure wave velocity with an interface pressure sensor system, such as described herein. As with the method of FIG. 7, the method of this figure can be performed by any suitable hardware, software, analog circuitry, or any combination or interoperation thereof. This description is not repeated.

Generally and broadly, FIG. 9 corresponds to a method of determining wave velocity by sampling two sensors separated by a known distance. In particular the method 900 includes operation 902 at which a first interface pressure sensor module is sampled. Next at operation 904, a second interface pressures sensor module is sample. Finally, at operation 906, the method 900 advances to correlate a first pressure wave obtained by the first pressure sensor to a second pressure wave obtained by the second pressure sensor. Based on this correlation, wave velocity between the two pressure sensors can be determined.

Figure 10:
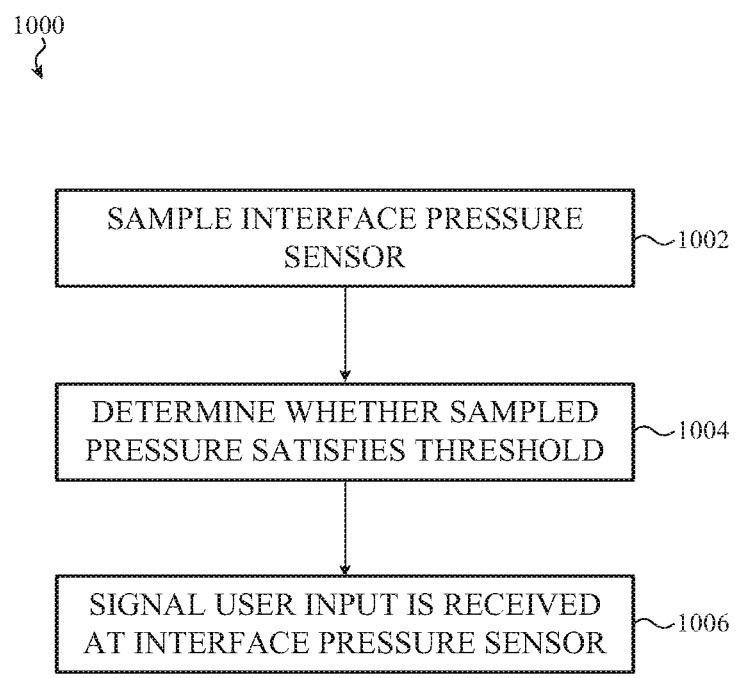
FIG. 10 is a flowchart depicting example operations of a method of receiving user input an interface pressure sensor system, such as described herein.

FIG. 10 is a flowchart depicting example operations of a method of receiving user input an interface pressure sensor system, such as described herein. As with the method of FIG. 7, the method of this figure can be performed by any suitable hardware, software, analog circuitry, or any combination or interoperation thereof. This description is not repeated.

The method 1000 includes operation 1002 in which a pressure module is sampled. Next, at operation 1004, the sample is compared against a threshold to determine whether signal(s) output from the sensor satisfy a threshold. At operation 1006, upon determining that the sensor does satisfy the threshold, the method 1000 can signal that a user input has been received. More generally and broadly, FIG. 10 corresponds to a method of rejecting low-magnitude inputs or high-intensity inputs to a computing device by leveraging an interface pressure sensing system, as described herein.

Figure 11:
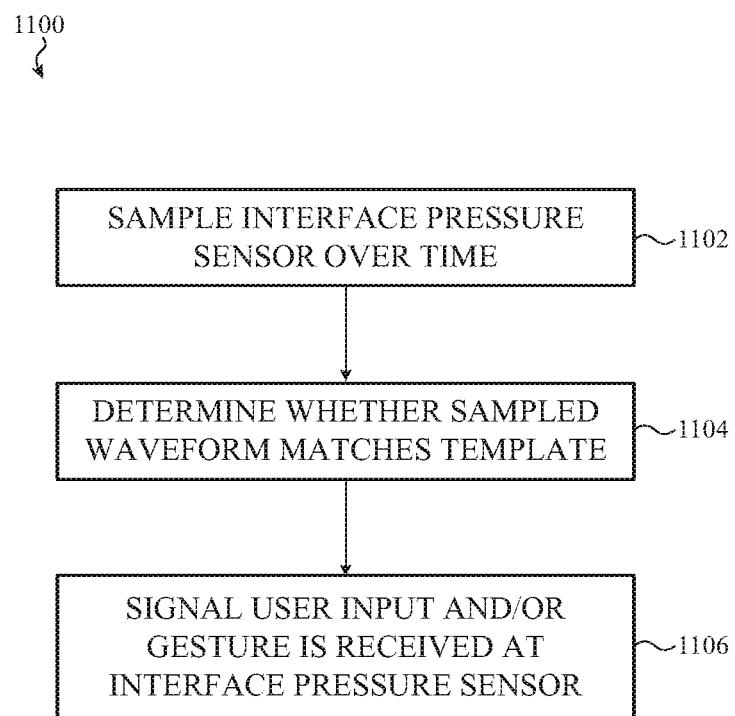
FIG. 11 is a flowchart depicting example operations of another method of receiving user input an interface pressure sensor system, such as described herein.

FIG. 11 is a flowchart depicting example operations of another method of receiving user input an interface pressure sensor system, such as described herein. As with the method of FIG. 7, the method of this figure can be performed by any suitable hardware, software, analog circuitry, or any combination or interoperation thereof. This description is not repeated.

The method 1100 includes operation 1102 at which a pressure sensor module of an interface pressure sensor system, as described herein, is sampled. Next, at operation 1104, the waveform obtained from the sensor can be compared against a set of template waveforms to determine whether the waveform matches a known waveform type. Thereafter, upon determining that the waveform matches a particular waveform type or template, a user input can be signaled at operation 1106. Generally and broadly, FIG. 11 corresponds to a method of receiving force input to an electronic device in the form of gestures, such as single tap gestures, multi-tap gestures, pattern-tap gestures, and so on.

Figure 12:
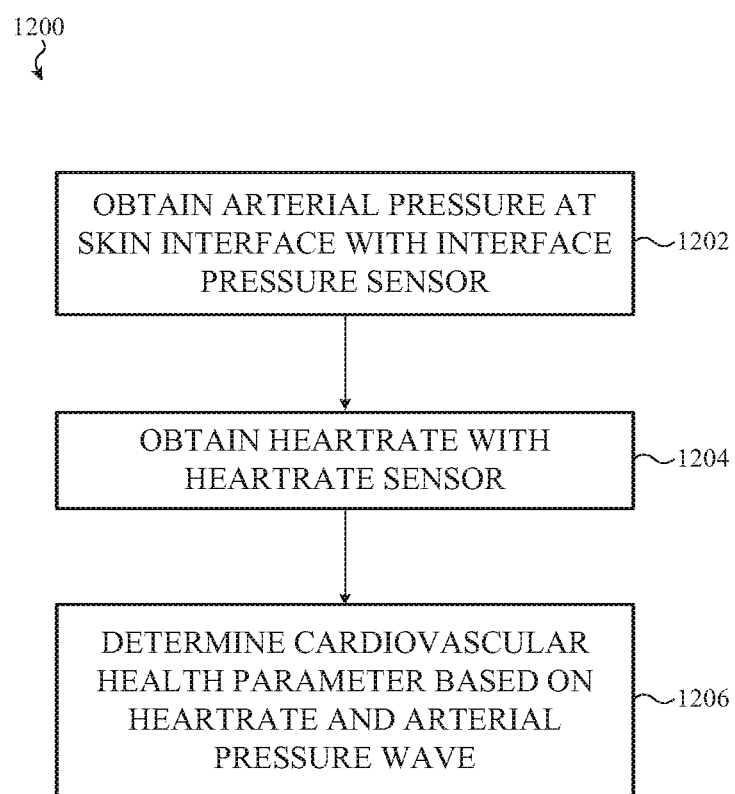
FIG. 12 is a flowchart depicting example operations of a method of non-invasively determining blood pressure of a user by leveraging an output of an interface pressure sensor system, such as described herein.

FIG. 12 is a flowchart depicting example operations of a method of non-invasively determining blood pressure of a user by leveraging an output of an interface pressure sensor system, such as described herein. As with the method of FIG. 7, the method of this figure can be performed by any suitable hardware, software, analog circuitry, or any combination or interoperation thereof. This description is not repeated.

The method 1200 includes operation 1202 at which an arterial pressure wave is obtained by leveraging output from an interface pressure sensor system positioned in contact with the skin of a user's wrist, above that user's radial artery. Next, at operation 1204, a heartrate can be obtained from a heart rate sensor, such as a photoplethysmographic sensor or an electrocardiogram sensor. Finally at operation 1206, a cardiovascular health parameter can be determined by leveraging both the user's heart rate and blood pressure. An example health parameter may be, without limitation: augmentation index; systolic blood pressure; diastolic blood pressure; median blood pressure; and so on.

Generally and broadly, FIG. 12 corresponds to a method of combining multiple biometric sensor outputs into a single diagnostic or health information output. In other cases, different types of sensors outputs may be leveraged including, but not limited to: temperature sensors; accelerometers; acoustic sensors; ultraviolet sensors; moisture sensors; sweat content sensors; and so on.

Figure 13:
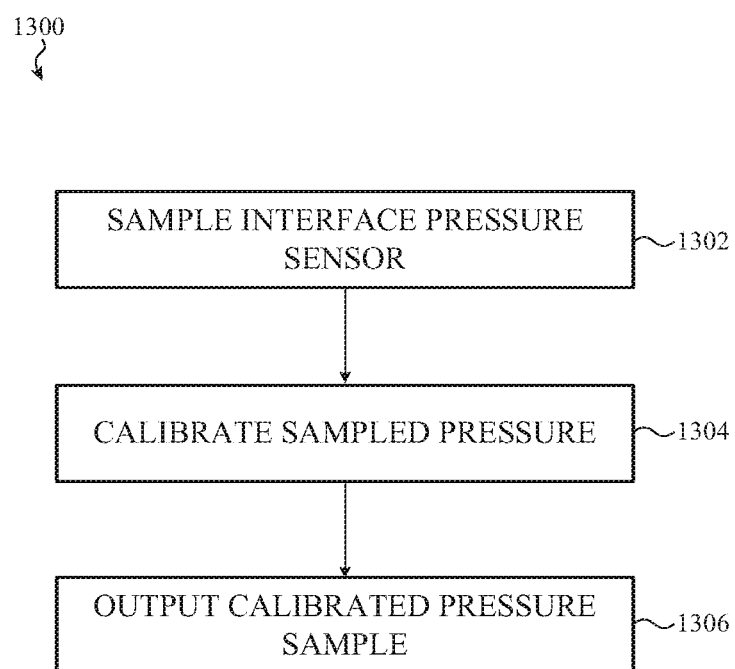
FIG. 13 is a flowchart depicting example operations of a method of calibrating an output of an interface pressure sensor system, such as described herein.

FIG. 13 is a flowchart depicting example operations of a method of calibrating an output of an interface pressure sensor system, such as described herein. As with the method of FIG. 7, the method of this figure can be performed by any suitable hardware, software, analog circuitry, or any combination or interoperation thereof. This description is not repeated.

The method 1300 includes operation 1302 at which an interface pressure sensor module, as described herein is sampled to obtain a waveform. Next, at operation 1304, an output of the interface pressure sensor module (e.g., the samples obtained at operation 1302) can be calibrated based on an output of another sensor, system, or lookup table. For example, an output from a temperature sensor can be used to adjust the output of the interface pressure sensor to account for thermal sensitivity of that interface sensor. In another example, a factory-calibration lookup table can be accessed and an output from the sensor can be biased or otherwise adjusted accordingly. Finally, at operation 1306, calibrated output can be provided to another circuit or system.

Figure 14:
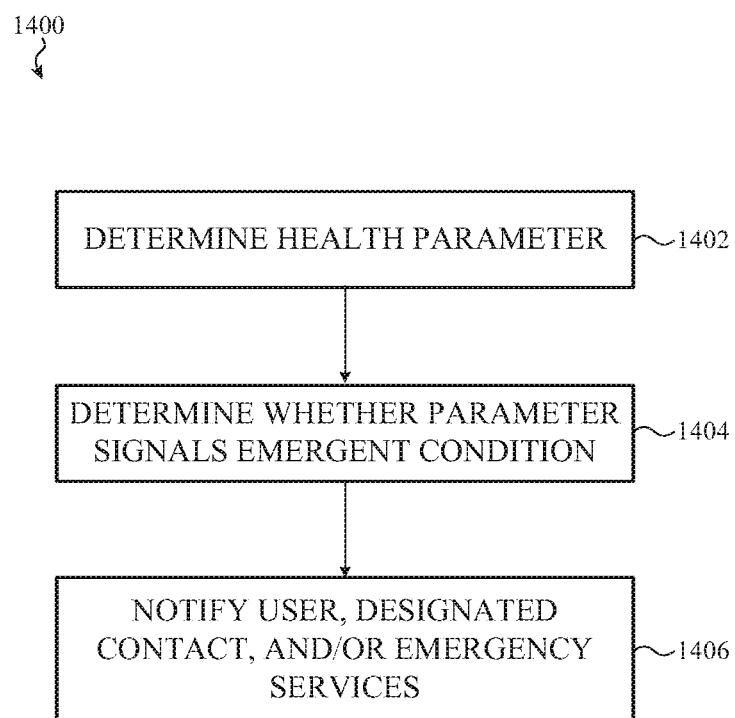
FIG. 14 is a flowchart depicting example operations of a method of leveraging output of an interface pressure sensor system, such as described herein.

FIG. 14 is a flowchart depicting example operations of a method of leveraging output of an interface pressure sensor system, such as described herein. As with the method of FIG. 7, the method of this figure can be performed by any suitable hardware, software, analog circuitry, or any combination or interoperation thereof. This description is not repeated.

The method 1400 generally and broadly corresponds to a method of quickly reacting to an emergent health condition based on output from an interface pressure sensor such as described herein. In particular, the method 1400 includes operation 1402 at which a health parameter is determined (e.g., blood pressure, respiration rate, movement, and so on). Next, at operation 1404, it may be determined whether that health parameter is indicative or diagnostic of an emergent condition. For example, a sudden drop or increase in blood pressure may signal an emergent condition. Similarly, an elevated heart rate detected without corresponding movement or motion may signal tachycardia or another emergent condition. In response to determining that an emergent condition may be likely, the method 1400 can advance to trigger one or more verification routines that can attempt to verify or collect additional information about or during the emergent condition. In addition, at operation 1406, the user, or a designated emergency contact, and/or emergency services can be notified of the detected emergent condition.

These foregoing embodiments depicted in FIGS. 7-14 and the various alternatives thereof and variations thereto are presented, generally, for purposes of explanation, and to facilitate an understanding of various configurations and constructions of a system, such as described herein. However, it will be apparent to one skilled in the art that some of the specific details presented herein may not be required in order to practice a particular described embodiment, or an equivalent thereof.

Thus, it is understood that the foregoing and following descriptions of specific embodiments are presented for the limited purposes of illustration and description. These descriptions are not targeted to be exhaustive or to limit the disclosure to the precise forms recited herein. To the contrary, it will be apparent to one of ordinary skill in the art that many modifications and variations are possible in view of the above teachings.

As used herein, the phrase "at least one of" preceding a series of items, with the term "and" or "or" to separate any of the items, modifies the list as a whole, rather than each member of the list. The phrase "at least one of" does not require selection of at least one of each item listed; rather, the phrase allows a meaning that includes at a minimum one of any of the items, and/or at a minimum one of any combination of the items, and/or at a minimum one of each of the items. By way of example, the phrases "at least one of A, B, and C" or "at least one of A, B, or C" each refer to only A, only B, or only C; any combination of A, B, and C; and/or one or more of each of A, B, and C. Similarly, it may be appreciated that an order of elements presented for a conjunctive or disjunctive list provided herein should not be construed as limiting the disclosure to only that order provided.

One may appreciate that although many embodiments are disclosed above, that the operations and steps presented with respect to methods and techniques described herein are meant as exemplary and accordingly are not exhaustive. One may further appreciate that alternate step order or fewer or additional operations may be required or desired for particular embodiments.

Although the disclosure above is described in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the some embodiments of the invention, whether or not such embodiments are described and whether or not such features are presented as being a part of a described embodiment. Thus, the breadth and scope of the present invention should not be limited by any of the above-described exemplary embodiments but is instead defined by the claims herein presented.

As described above, one aspect of the present technology is determining various input and health parameters, and the like. The present disclosure contemplates that in some instances this gathered data may include personal information data that uniquely identifies or can be used to contact or locate a specific person. Such personal information data can include demographic data, location-based data, telephone numbers, email addresses, twitter IDs (or other social media aliases or handles), home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to provide haptic or audiovisual outputs that are tailored to the user. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act ("HIPAA"); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of determining spatial parameters, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, haptic outputs may be provided based on non-personal information data or a bare minimum amount of personal information, such as events or states at the device associated with a user, other non-personal information, or publicly available information.

What is claimed is:
1. An electronic device configured for biometric sensing, the electronic device comprising:
 a sensing surface configured to detect pressure variations deforming an external surface of an object; and an interface pressure sensing system at least partially defining the sensing surface, the interface pressure sensing system comprising:
a stiffener;
a substrate supported by the stiffener;
a first pressure sensing module disposed on the substrate and comprising:
a first frame coupled to the substrate and defining a first volume;
a first fluid pressure sensor disposed within the first volume; and
a first infill encapsulating the first fluid pressure sensor within the first volume and at least partially defining the sensing surface; and
a second pressure sensor module disposed on the substrate, offset from the first pressure sensing module and comprising:
a second frame coupled to the substrate and defining a second volume;
a second fluid pressure sensor disposed within the second volume; and
a second infill encapsulating the second fluid pressure sensor within the second volume and at least partially defining the sensing surface; and
a third frame coupled to the substrate defining a third volume enclosing the first pressure sensing module and the second pressure sensing module, the third volume filled by a third infill encapsulating the first pressure sensing module and the second pressure sensing module and at least partially defining the sensing surface.

2. The electronic device of claim 1, further comprising a processor operably coupled to the interface pressure sensing system and operable to:
receive a first output from the first fluid pressure sensor; and
receive a second output from the second fluid pressure sensor.

3. The electronic device of claim 2, wherein:
the object is a user of the electronic device;
the external surface is an epidermis region of the user.

4. The electronic device of claim 3, wherein the processor is configured to determine an augmentation index of the user based on at least one of the first output or the second output.

5. The electronic device of claim 3, wherein the processor is configured to determine at least one of a systolic or a diastolic blood pressure of the user based on at least one of the first output or the second output.

6. The electronic device of claim 3, wherein the processor is configured to determine an arterial state of the user based on at least one of the first output or the second output.

7. The electronic device of claim 3, further comprising:
a heartrate sensor operably coupled to the processor, the heartrate sensor configured to provide a third output; wherein:
the processor is configured to determine a health parameter of the user based on the third output and at least one of the first output or the second output.

8. The electronic device of claim 7, wherein the health parameter is selected from a group consisting of:
augmentation index;
chronological age;
arterial age state;
arterial disease state; and
user stress level.

9. The electronic device of claim 1, wherein the sensing surface defines at least a portion of an interior surface of a band worn on a user's wrist.

10. The electronic device of claim 1, comprising:
a housing configured to be supported by at least a portion of an ear of a user; and
the sensing surface defines at least a portion of an exterior surface of the housing configured to contact skin.

11. The electronic device of claim 1, wherein:
the stiffener is formed from metal;
the first frame is formed from metal; and
the second frame is formed from metal.

* * * * *